(12) United States Patent
Flood et al.

(10) Patent No.: US 10,202,395 B2
(45) Date of Patent: Feb. 12, 2019

(54) MACROCYCLE WITH REPEATING TRIAZOLE-CARBAZOLE UNITS

(71) Applicant: INDIANA UNIVERSITY RESEARCH & TECHNOLOGY CORPORATION, Indianapolis, IN (US)

(72) Inventors: Amar Flood, Bloomington, IN (US); Brandon E. Hirsch, Bloomington, IN (US); Semin Lee, Urbana, IL (US); Steven L. Tait, Bloomington, IN (US); James Dobscha, Brunswick, OH (US)

(73) Assignee: Indiana University Research & Technology Corporation, Indianapolis, IN (US)

( * ) Notice: Subject to any disclaimer, the term of this patent is extended or adjusted under 35 U.S.C. 154(b) by 323 days.

(21) Appl. No.: 15/170,677

(22) Filed: Jun. 1, 2016

(65) Prior Publication Data
US 2016/0347758 A1   Dec. 1, 2016

Related U.S. Application Data

(60) Provisional application No. 62/169,451, filed on Jun. 1, 2015.

(51) Int. Cl.
*C07D 487/22* (2006.01)
*C02F 1/68* (2006.01)
(Continued)

(52) U.S. Cl.
CPC ......... *C07D 487/22* (2013.01); *B01D 15/363* (2013.01); *B01J 20/22* (2013.01);
(Continued)

(58) Field of Classification Search
None
See application file for complete search history.

(56) References Cited

U.S. PATENT DOCUMENTS

2012/0270141 A1* 10/2012 Koshino ............... B01J 31/183
429/492

OTHER PUBLICATIONS

Li and Flood (Angewandte Chemie, 2008, 47, 2649-2652). (Year: 2008).*

(Continued)

*Primary Examiner* — Clare M Perrin
(74) *Attorney, Agent, or Firm* — Klintworth & Rozenblat IP LLC

(57) ABSTRACT

Disclosed herein are compositions of tricarbazole triazolophane (tricarb) of Formulas (I), (II) and (III):

(Continued)

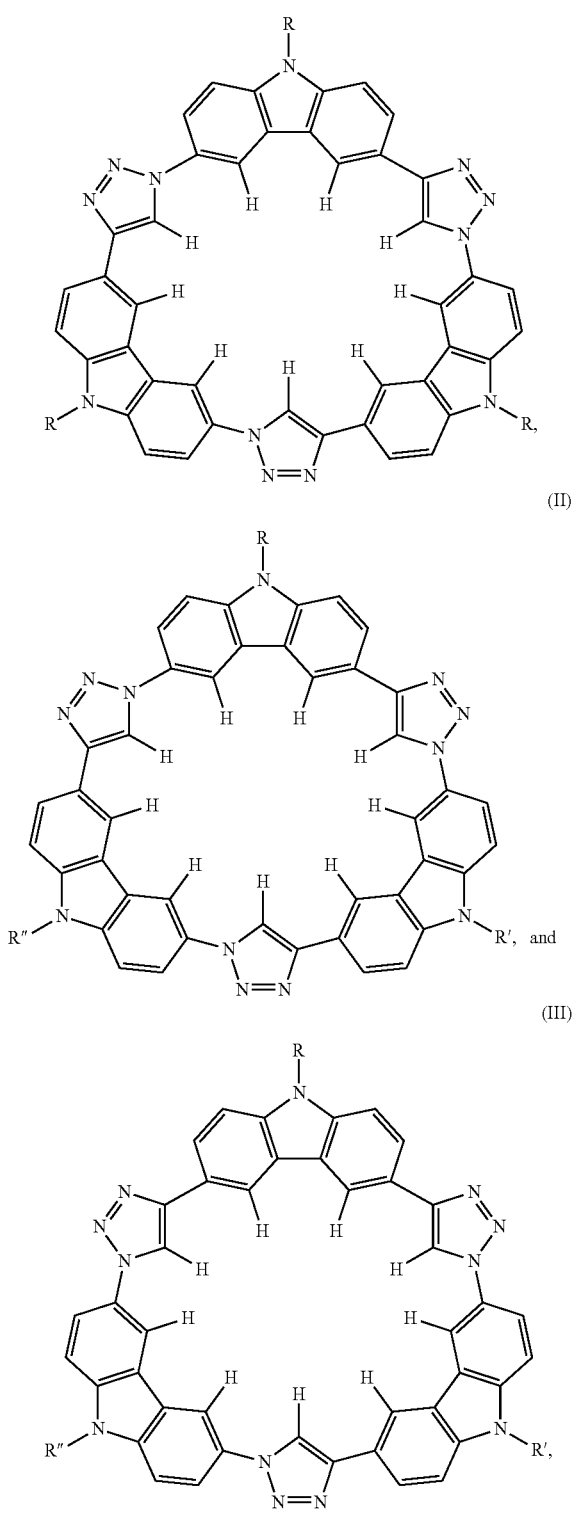

wherein R of Formula (I) is selected from a group consisting of alkyl (for example, $C_6$-$C_{18}$), alkyl-substituted phenyl derivatives, and substituted glycol derivatives, among others, or a combination thereof, and R, R' and R" of Formulas (II) and (III) are independently selected from a group consisting of alkyl (for example, $C_6$ to $C_{18}$), alkyl-substituted phenyl derivatives, and substituted glycol derivatives, or a combination thereof. The disclosure presents examples of thin films composed of the same as well as methods of binding anions from the same.

19 Claims, 8 Drawing Sheets

(51) Int. Cl.

| | | |
|---|---|---|
| B01J 47/12 | (2017.01) | |
| B01J 45/00 | (2006.01) | |
| B01J 20/22 | (2006.01) | |
| B01D 15/36 | (2006.01) | |
| B01J 41/04 | (2017.01) | |
| C02F 1/42 | (2006.01) | |
| B01J 41/09 | (2017.01) | |
| C02F 101/12 | (2006.01) | |
| C02F 103/00 | (2006.01) | |

(52) U.S. Cl.
CPC ............... *B01J 41/04* (2013.01); *B01J 41/09* (2017.01); *B01J 45/00* (2013.01); *B01J 47/12* (2013.01); *C02F 1/42* (2013.01); *C02F 1/683* (2013.01); *C02F 2001/422* (2013.01); *C02F 2101/12* (2013.01); *C02F 2103/007* (2013.01)

(56) References Cited

OTHER PUBLICATIONS

Hua et al. (Chemistry, 2011, 17, 312-321). (Year: 2011).*
Adam, et al., "Fast photoconduction in th ehighly ordered columnar phase of a discotic liquid crystal," Nature 1994, 371, 141-143.
Blunt, et al., "Temperature-Induced Structural Phase Transitions in a Two-Dimensional Self-Assembled Network," J. Am. Chem. Soc. 2013, 135, 2068-12075.
Colson, et al., "Oriented 2D Covalent Organic Framework Thin Films on Single-Layer Graphene," Science 2011, 332, 228-232.
Finke, et al., "Engineering Solid-State Morphologies in Carbazole-Ethynylene Macrocycles,"J. Am. Chem. Soc. 2011, 133, 14063-14070.
Gorodetsky, et al., "Reticularted Heterojunctions for Photovoltaic Devices," Angew. Chem. Int. Ed. 2010, 49, 7909-7912.
Helsel, et al., "Highly Conducting Transmembrane Pores Formed by Aromatic Oligoamide Macrocycles," J. Am. Chem. Soc. 2008, 130, 15784-15785.
Hirsch, et al., "Selective Anion-Induced Crystal Switching and Binding in Surface Monolayers Modulated by Electric Fields from Scanning Probes," ACS Nano 2014, 8, 10858-10869.
Hirsch, et al., "Anion-induced dimerization of 5-fold symmetric cyanostars in 3D crystalline solids and 2D self-assembled crystals," Chem. Commun. 2014, 50, 9827-9830.
Hua, et al., "Aromatic and Aliphatic CH Hydrogen Bonds Fight for Chloride while Competing Alongside Ion Pairing within Triazolophanes," Chem. Eur. J. 2011, 17, 312-321.
Jenekhe, et al., "New Conjugated Polymers with Donor-Acceptor Architectures: Synthesis and Photophysics of Carbazole-Quinoline and Phenothiazine-Quuinoline Copolymers and Oligomers Exhibiting Large Intramolecular Charge Transfer," Macromolecules 2001, 34, 7315-7324.
Kato, et al., "Functional Liquid-Crystalline Assemblies: Self-Organized Soft Materials," Angew. Chem. Int. Ed. 2006, 45, 38-68.
Langner, et al., "Two- to one-dimensional transition of self-assembled coordination networks at surfaces by organic ligand addition," Chem. Commun. 2009, 2502-2504.
Lee, et al., "Forced to Align: Flow-Induced Long-Range Alignment of Hierarchical Molecular Assemblies from 2D to 3D," J. Am. Chem. Soc. 2014, 136, 4117-4120.

(56) References Cited

OTHER PUBLICATIONS

Lee, et al., "A pentagonal cyanostar macrocycle with cyanostilbene CH donors binds anions and forms dialkylphosphate [3]rotaxanes," Nat. Chem. 2013, 5, 704-710.

Li, et al., "Pure C—H Hydrogen Bonding to Chloride Ions: A Preorganized and Rigid Macrocyclic Receptor," Angew. Chem. Int. Ed. 2008, 47, 2649-2652.

Mamdouh, et al., "Solvent Controlled Self-Assembly at the Liquid-Solid Interface Revealed by STM," J. Am. Chem. Soc. 2005, 128, 317-325.

Marie, et al., "Tuning the Packing Density of 2D Supramolecular Self-Assemblies at the Solid-Liquid Interface Using Variable Temperature," ACS Nano 2010, 4, 1288-1292.

Martin, "Comparisons of Indefinite Self-Association Models," Chem. Rev. 1996, 96(8), 3043-3064.

Okochi, et al., "Covalent Assembly of Heterosequenced macrocycles and Molecular Cages through Orthogonal Dynamic Covalent Chemistry (ODCC)," Org. Lett. 2013, 15, 4296-4299.

Piot, et al., "Hierarchical Self-Assembly of Edge-On Nanocolumnar Superstructures of Large Disc-Like Molecules," Adv. Mater 2008, 20, 3854-3858.

Quinn, et al., "Does the A-T or G-C Base-Pair Possess Enhanced Stability? Quantifying the Effects of CH•••O Interactions and Secondary Interactions on Base-Pair Stability Using a Phenomenological Analysis and ab Initio Calculations," J. Am. Chem. Soc. 2007, 129, 934-941.

Roobottom, et al., "Thermochemical Radii of Complex Ions" J. Chem. Ed. 1999, 76, 1570-1573.

Rosenthal, "The Myth of the Non-Coordinating Anion," J. Chem. Ed. 1973, 50, 331-335.

Samori, et al., "Epitaxial Composite Layers of Electron Donors and Acceptors from Very Large Polycyclic Aromatic Hydrocarbons," J. Am. Chem. Soc. 2002, 124, 9454-9457.

Skomski, et al., "High-Fidelity Self-Assembly of Crystalline and Parallel-Oriented Organic Thin Films by π-π Stacking from a metal Surface," Langmuir 2014, 30, 10050-10056.

Vander Griend, et al., "Detailed Spectroscopic, Thermodynamic, and Kinetic Characterization of Nickel(II) Complexes with 2,2'-Bipyridine and 1,10-Phenanthroline Attained via Equilibrium-Restricted Factor Analysis," Inorg. Chem. 2008, 47, 656-662.

Wheeler, et al., "Toward a More Complete Understanding of Noncovalent Interactions Involving Aromatic Rings," J. Phys. Chem. A 2014, 118, 6133-6147.

Zhang, et al., "Shape-Persistent Macrocycles: Structures and Synthetic Approaches from Arylene and Ethynylene Building Blocks," Angew. Chem. Int. Ed. 2006, 45, 4416-4439.

\* cited by examiner

MACROCYCLE WITH REPEATING TRIAZOLE-CARBAZOLE UNITS

CROSS-REFERENCE TO RELATED APPLICATIONS

This application claims benefit of priority under 35 U.S.C. 119 to U.S. provisional patent application Ser. No. 62/169,451, filed Jun. 1, 2015, and entitled "NOVEL MACROCYCLE WITH REPEATING TRIAZOLE-CARBAZOLE UNITS," the contents of which are herein incorporated by reference in its entirety.

BACKGROUND

1. Technical Field

The present disclosure relates to macrocycle structures having triazole-carbazole units configured to bind large anions.

2. Description of Related Art

Considerable interest exists for removing hazardous chemical ions from the environment, such as large anions. Large anions are hard to bind and present significant environmental hazards. Few examples of charge-neutral chelators exist that can bind larger anions like these with such high affinities. For example, perchlorate ($ClO_4^-$) is a large anion by-product of munitions and jet propulsion that is an acute environmental hazard as it accumulates in waterways such as the Colorado River. Perchlorate presents a human health risk as it interferes with thyroid hormone biosynthesis and thus impacts how energy is managed in the body. Current approaches to removing $ClO_4^-$ make use of ion-exchange resins, either single-use or recyclable, and each has its pros and cons. But, they share issues with the level of $ClO_4^-$ that can be removed (the actual value of the cleaned water efflux from the ion-exchange beds is sometimes below the limit of detection). There is a need for new reagents to allow detection and removal of $ClO_4^-$ to lower levels in efflux water.

In certain research and industrial applications with ion-exchange processes, the unwanted removal of sulfate that competes with adsorption sites to lower the $ClO_4^-$ capacity of the ion-exchange resin. Furthermore, those exchange resins rely upon cationic sites for exchanging anions for $ClO_4^-$. Thus, it has not been possible to use neutral organic molecule receptors that are capable of chelating anions like $ClO_4^-$. Such organic molecule receptors that are specifically designed for large anions like $ClO_4^-$ have not been targeted. This situation is likely a result of the long-accepted idea that such anions are only weakly coordinating (M. R. Rosenthal, *J. Chem. Ed.* 1973, 50, 331-335). Thus, there is a need for new compounds with a variety of chemical sequences to exquisitely tune the properties or usage for binding large anions like $ClO_4^-$ Furthermore, most anion-capture receptors are molecules that do not organize into thin films, which might offer certain advantages as an absorbant or sensory material.

Shape persistent macrocycles are attractive multifunctional molecules bearing inner cavities to bind guests (such as the aforementioned large anions) and outer surfaces to direct hierarchical self-assembly. While guest recognition has a rich history, the assembly of macrocycles and the supramolecular information that needs to be encoded into their surfaces to direct their self-organization is of ongoing interest. Examples include liquid-crystalline ordering of crown ethers for ion conduction (T. Kato, N. Mizoshita, K. Kishimoto, *Angew. Chem. Int. Ed.* 2006, 45, 38-68), pore-forming stacks of amido macrocycles for ion transport across membranes (A. J. Helsel, A. L. Brown, K. Yamato, W. Feng, L. Yuan, A. J. Clements, S. V. Harding, G. Szabo, Z. Shao, B. Gong, *J. Am. Chem. Soc.* 2008, 130, 15784-15785), and organized nanostructures for organic electronics (D. Adam, P. Schuhmacher, J. Simmerer, L. Haussling, K. Siemensmeyer, K. H. Etzbachi, H. Ringsdorf, D. Haarer, *Nature* 1994, 371, 141-143; A. A. Gorodetsky, C.-Y. Chiu, T. Schiros, M. Palma, M. Cox, Z. Jia, W. Sattler, I. Kymissis, M. Steigerwald, C. Nuckolls, *Angew. Chem. Int. Ed.* 2010, 49, 7909-7912). The informed design of macrocycles therefore requires parallel consideration of multiple design criteria. These designs also benefit from building blocks that can aid macrocycle synthesis (W. Zhang, J. S. Moore, *Angew. Chem. Int. Ed.* 2006, 45, 4416-4439).

BRIEF SUMMARY

In a first aspect, a composition including a tricarbazole triazolophane (tricarb) selected from one of the following is presented:

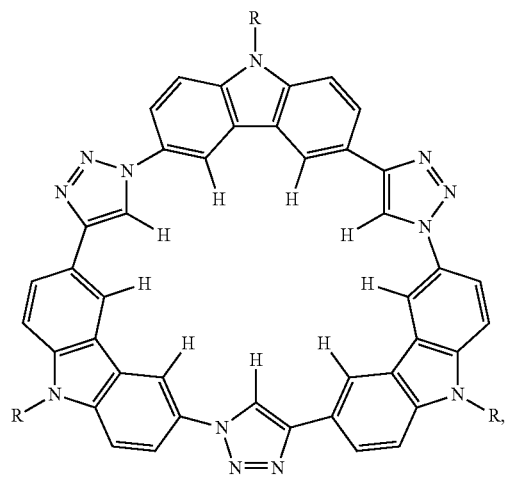

(I)

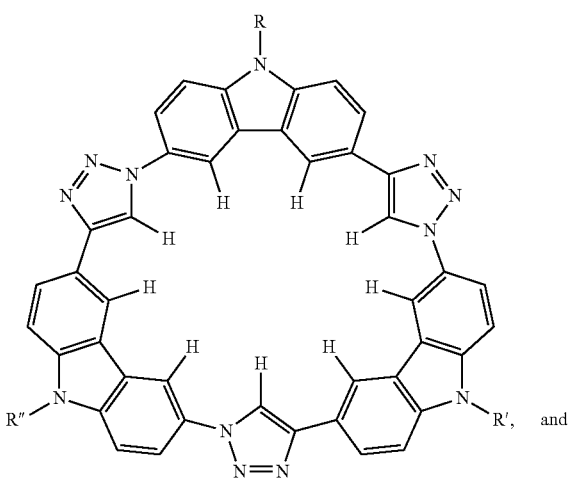

(II) and

-continued (III)

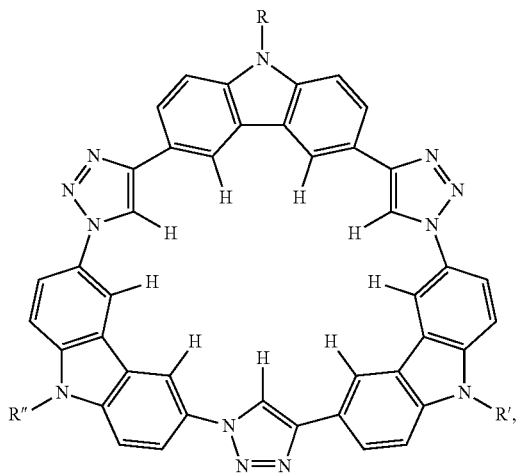

or a combination thereof,
wherein R of Formula (I) is selected from a group consisting of alkyl (for example, $C_6$ to $C_{18}$), alkyl-substituted phenyl derivatives, and substituted glycol derivatives, among others, or a combination thereof, and R, R' and R" of Formulas (II) and (III) is independently selected from a group consisting of alkyl (for example, $C_6$ to $C_{18}$), alkyl-substituted phenyl derivatives, and substituted glycol derivatives, among others, or a combination thereof.

In a second aspect, a method of binding an anion is provided. The method includes the step of contacting the anion with the composition as described in the first aspect.

In a third aspect, a method of removing an anion from a mixture is provided. The method includes at least two steps. The first step includes contacting the mixture with the composition according the first aspect to form a complex of the anion with the composition of the first aspect. The second step includes separating the complex from the mixture.

In a fourth aspect, a thin film is provided. The thin film includes the composition according to the first aspect.

In a fifth aspect, a method of binding an anion is provided. The method includes a step of contacting the anion with a thin film according to the fourth aspect.

In a sixth aspect, a method of removing an anion from a mixture is provided. The method includes at least two steps. The first step includes contacting the mixture with a thin film according to the fourth aspect to form a complex of the anion and the thin film of the fourth aspect or a dissociated dimer of a tricarb thereof, wherein the tricarb comprises a composition of the first aspect. The second step includes separating from the mixture the complex of an anion and the thin film of the fourth aspect or a dissociated dimer of a tricarb thereof, wherein the tricarb comprises a composition of the first aspect.

In a seventh aspect, a method of controlling a thickness of the thin film of the fourth aspect is provided. The thickness of the thin firm is determined by at least one parameter selected from the group consisting of the following parameters: (i) varying a concentration of the composition of the first aspect; (ii) adding anions, and (iii) altering at least one substituent of the composition of the first aspect.

These and other features, objects and advantages of the present invention will become better understood from the description that follows. In the description, reference is made to the accompanying drawings, which form a part of the disclosure and in which there is shown by way of illustration, not limitation, embodiments of the invention.

BRIEF DESCRIPTION OF THE DRAWINGS

The features, objects and advantages other than those set forth above will become more readily apparent when consideration is given to the detailed description below. Such detailed description makes reference to the following drawings.

FIG. 4C: 150×$10^{-6}$ M, $I_T$=10 pA, $V_{sample}$=−0.5 V.

Figure 1:
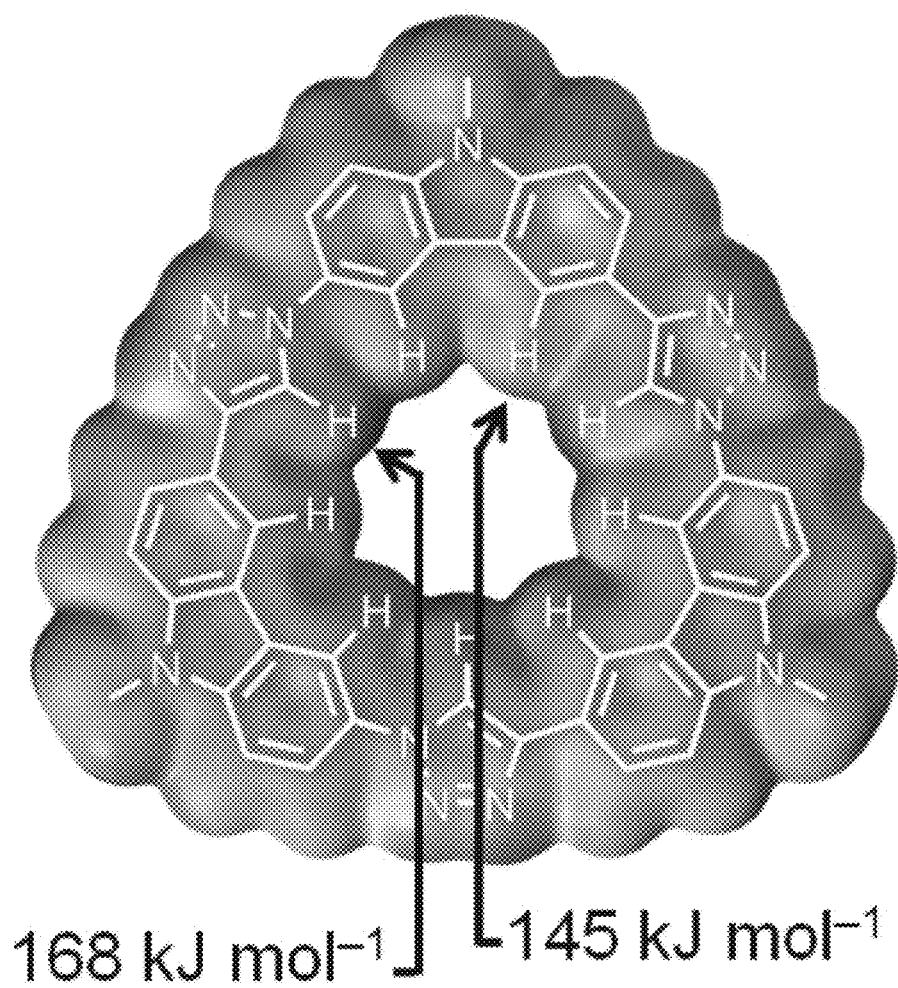
FIG. 1 depicts an exemplary electrostatic potential map of tricarb of Formula (I) (geometry optimized: B3LYP/6-31G*, red: −190 kJ $mol^{-1}$, blue: +170 kJ $mol^{-1}$).

While the present invention is amenable to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments and claims herein for interpreting the scope of the invention.

DETAILED DESCRIPTION

The compositions and methods now will be described more fully hereinafter with reference to the accompanying drawings, in which some, but not all permutations and variations of embodiments of the invention are shown. Indeed, the invention may be embodied in many different forms and should not be construed as limited to the embodiments set forth herein. These embodiments are provided in sufficient written detail to describe and enable one skilled in the art to make and use the invention, along with disclosure of the best mode for practicing the invention, as defined by the claims and equivalents thereof.

Likewise, many modifications and other embodiments of the compositions and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

Overview

The design of macrocycles called tricarbazole triazolophanes ("tricarb") is presented herein. These novel macrocycles employ alternating carbazole building blocks and triazole linkages for achieving one-pot syntheses and anion binding. As a result of the encoding present in the outer edges and surfaces of the macrocycle provided by the alternating carbazoles and triazoles, a plurality of the novel macrocycles organize into a hierarchical self-organization resulting in the formation of stacked tubular films. The present disclosure provides exemplary macrocycle compositions, methods for their synthesis, their novel anion-binding properties, and thin films assembled from the macrocycles.

Compositions and Synthetic Routes

Compositions of the invention include tricarbs of Formula (I):

(I)

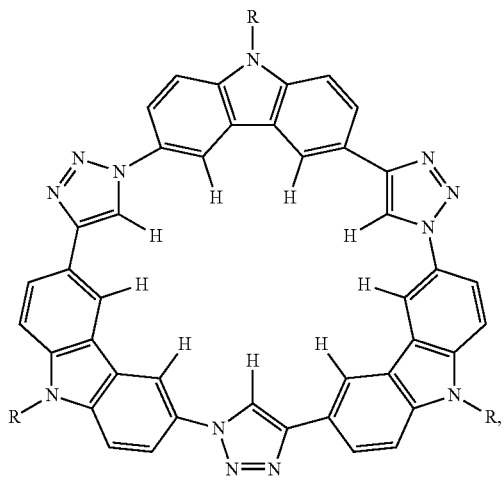

wherein R is selected from any substituent known in the art being compatible with forming a bond with nitrogen. For example, R can be a side chain having a net charge, such as positive (for example, amine-ammonium and pyridinium or negative (for example, carboxylates, sulfonates, among others) or R can be hydrophobic (for example, alkyls, aromatics, fluoroalkanes, among others). Thus, depending upon the chemical substituent for R, the resultant tricarb of Formula (I) can confer tunable solubility in water, organic solvents and fluorous solvents. Preferred compositions can include tricarbs of Formula (I), wherein R is alkyl (for example, $C_6$-$C_{18}$), alkyl-substituted phenyl derivatives, and substituted glycol derivatives, among others. Highly preferred compositions can include tricarbs of Formula (I), wherein R is $C_6H_{13}$ (IA) $C_{10}H_{21}$ (IB) $C_{18}H_{37}$ (IC), di-tert-butyl phenyl (ID) or triethylene glycol (IE):

(IA)

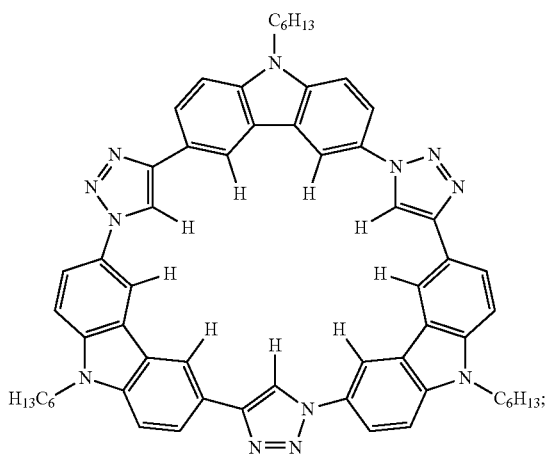

(IB)

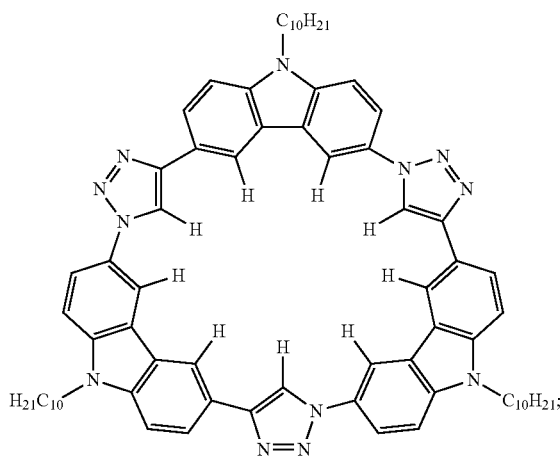

(IC)

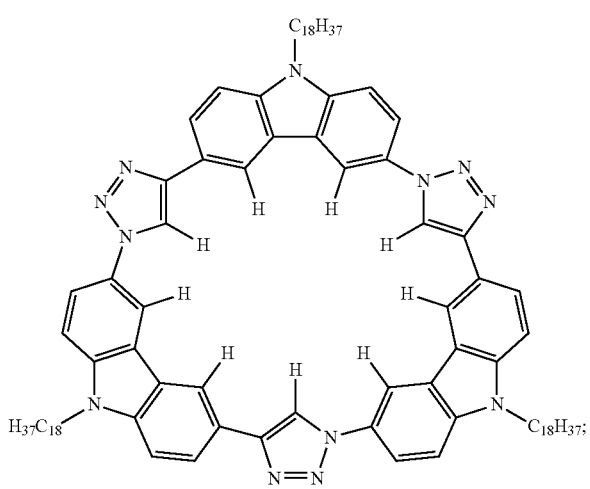

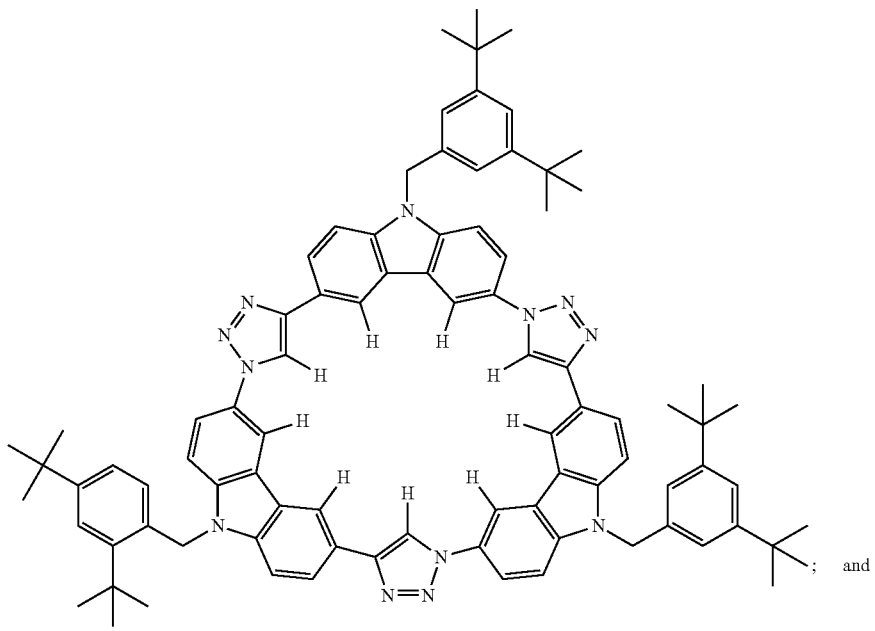
(ID)
and
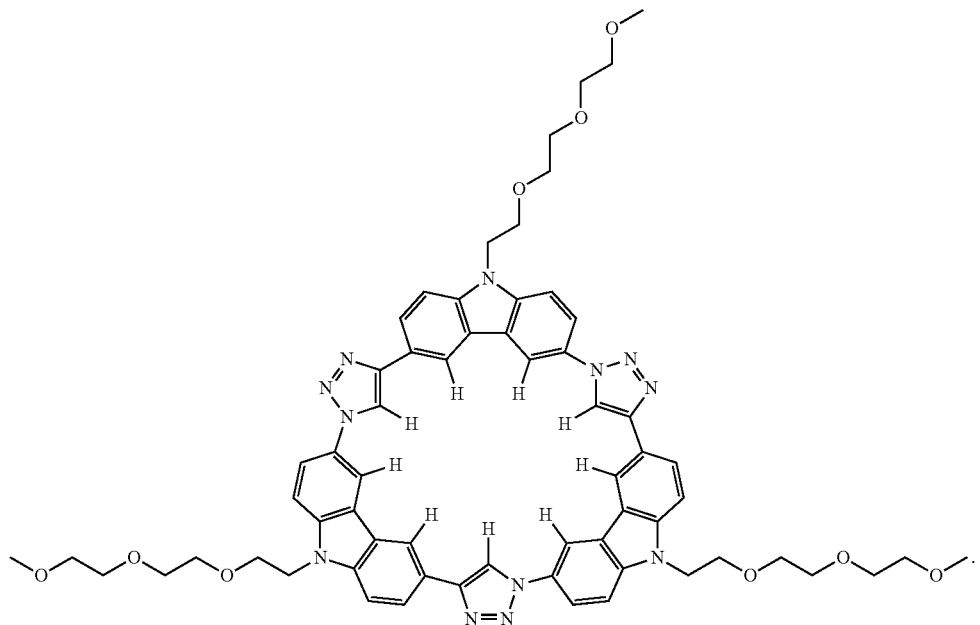
(IE)
A general synthetic route for preparing tricarbs of Formula (I) is presented in synthetic Scheme (A):
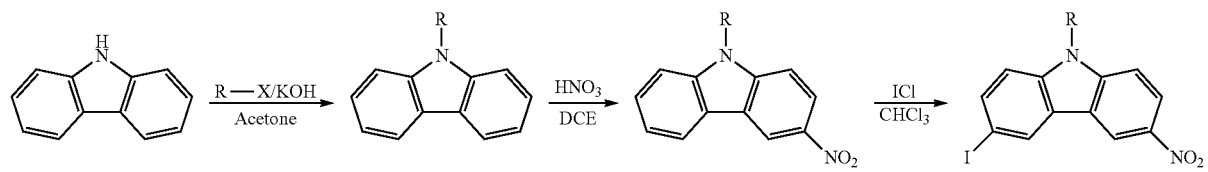
(A)

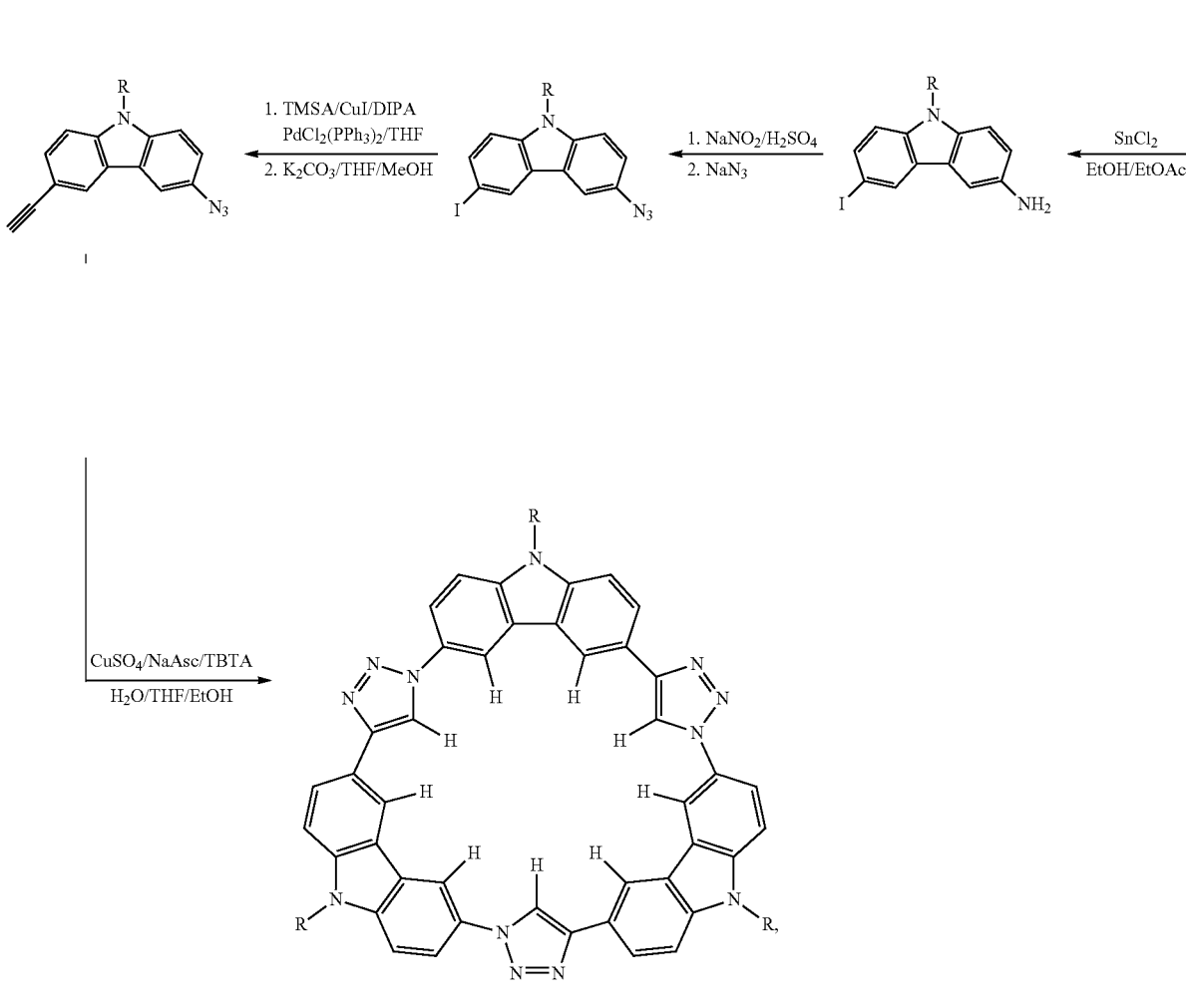

where R—X, where X includes a leaving group following a $S_N2$, such as, for example, a halide group (for example, $Br^-$, $Cl^-$, and $I^-$). Thus, tricarbs having the structure of Formula (I) can be prepared in a one-pot synthesis.

In another aspect, compositions of the invention include tricarbs of Formula (II):

(II)

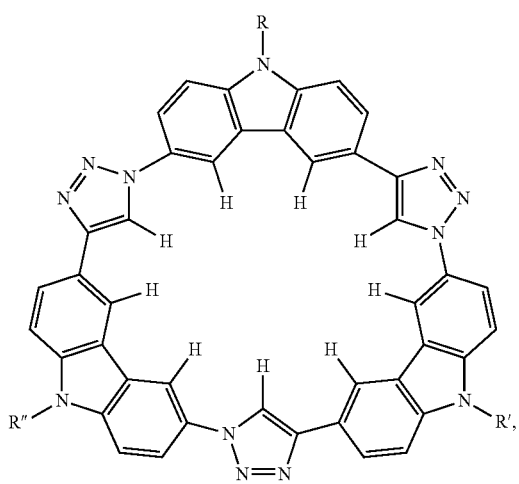

wherein R, R' and R" are independently selected from any substituent(s) known in the art being compatible with forming a bond with nitrogen. For example, R, R' and R" can be a side chain having a net charge, such as positive (for example, amine-ammonium and pyridinium or negative (for example, carboxylates, sulfonates, among others) or R, R' and R" can be hydrophobic (for example, alkyls, aromatics, fluoroalkanes, among others). Thus, depending upon the chemical substituent for R, R' and R", the resultant tricarb of Formula (II) can confer tunable solubility in water, organic solvents and fluorous solvents. Preferred compositions can include tricarbs of Formula (II) wherein R, R' and R" are independently selected from alkyl (for example, $C_6$-$C_{18}$), alkyl-substituted phenyl derivatives, and substituted glycol derivatives, among others.

One general, step-wise, synthetic route for preparing tricarbs of Formula (II) is presented in synthetic Scheme (B):

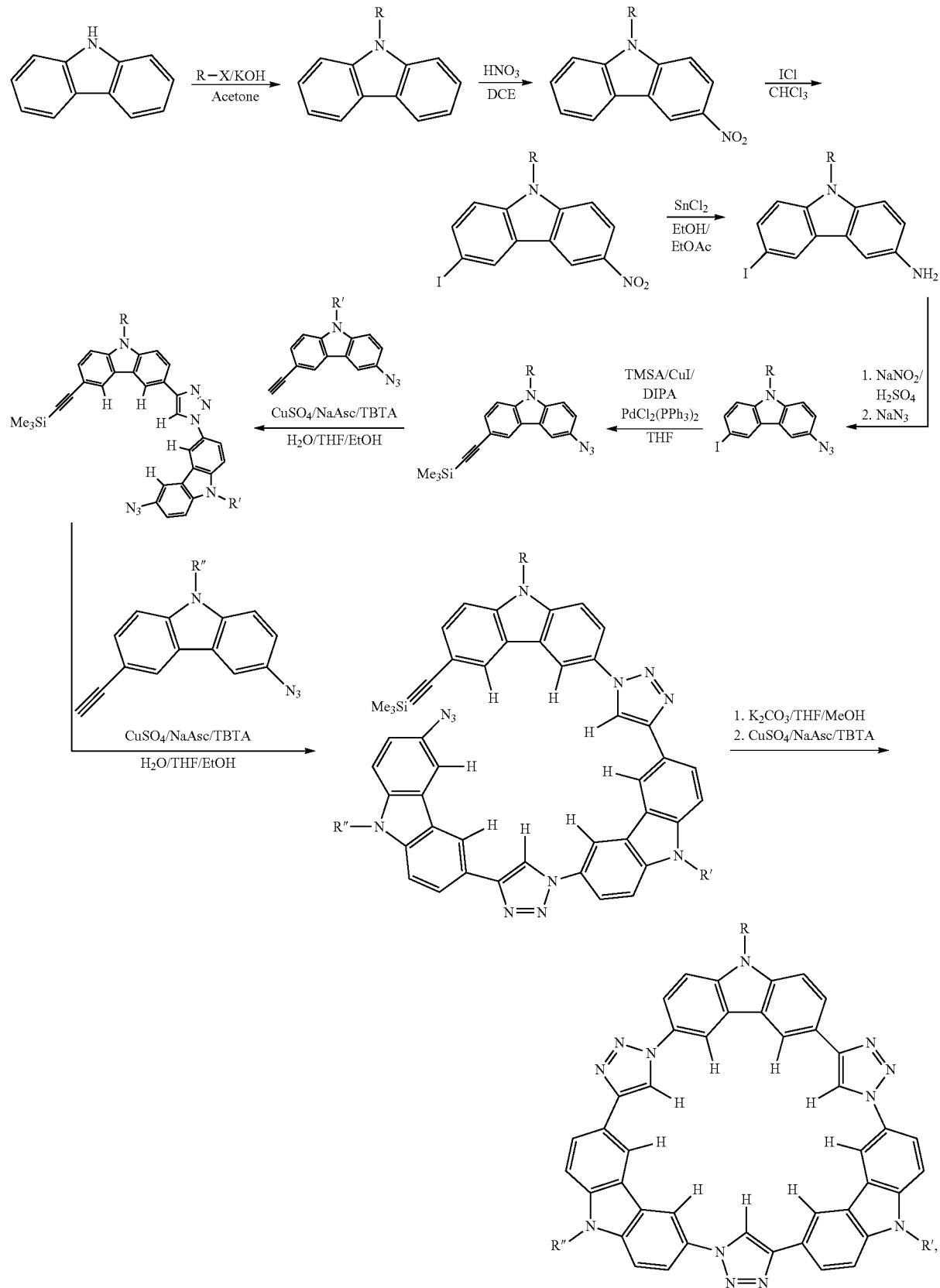

wherein compounds having R' and R" are used at 10 mol % in the designated synthesis steps using those compounds, owing to the statistical distribution analysis of the side chains in the expected products formed from the synthesis.

In another aspect, compositions of the invention include tricarbs of Formula (III):

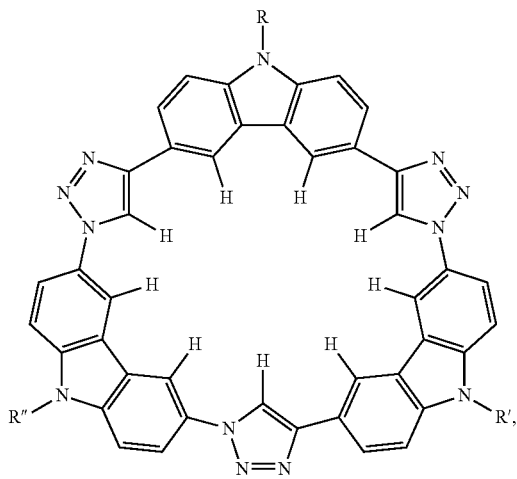

(III)

wherein R, R' and R" are independently selected from any substituent(s) known in the art being compatible with forming a bond with nitrogen. For example, R, R' and R" can be a side chain having a net charge, such as positive (for example, amine-ammonium and pyridinium or negative (for example, carboxylates, sulfonates, among others) or R, R' and R" can be hydrophobic (for example, alkyls, aromatics, fluoroalkanes, among others). Thus, depending upon the chemical substituent for R, R' and R", the resultant tricarb of Formula (III) can confer tunable solubility in water, organic solvents and fluorous solvents. Preferred compositions can include tricarbs of Formula (III) wherein R, R' and R" are independently selected from alkyl (for example, $C_6$-$C_{18}$), alkyl-substituted phenyl derivatives, and substituted glycol derivatives, among others.

A piece-wise, synthetic route for preparing tricarbs of Formulas (I)-(III) is presented in synthetic Scheme (C):

(C)
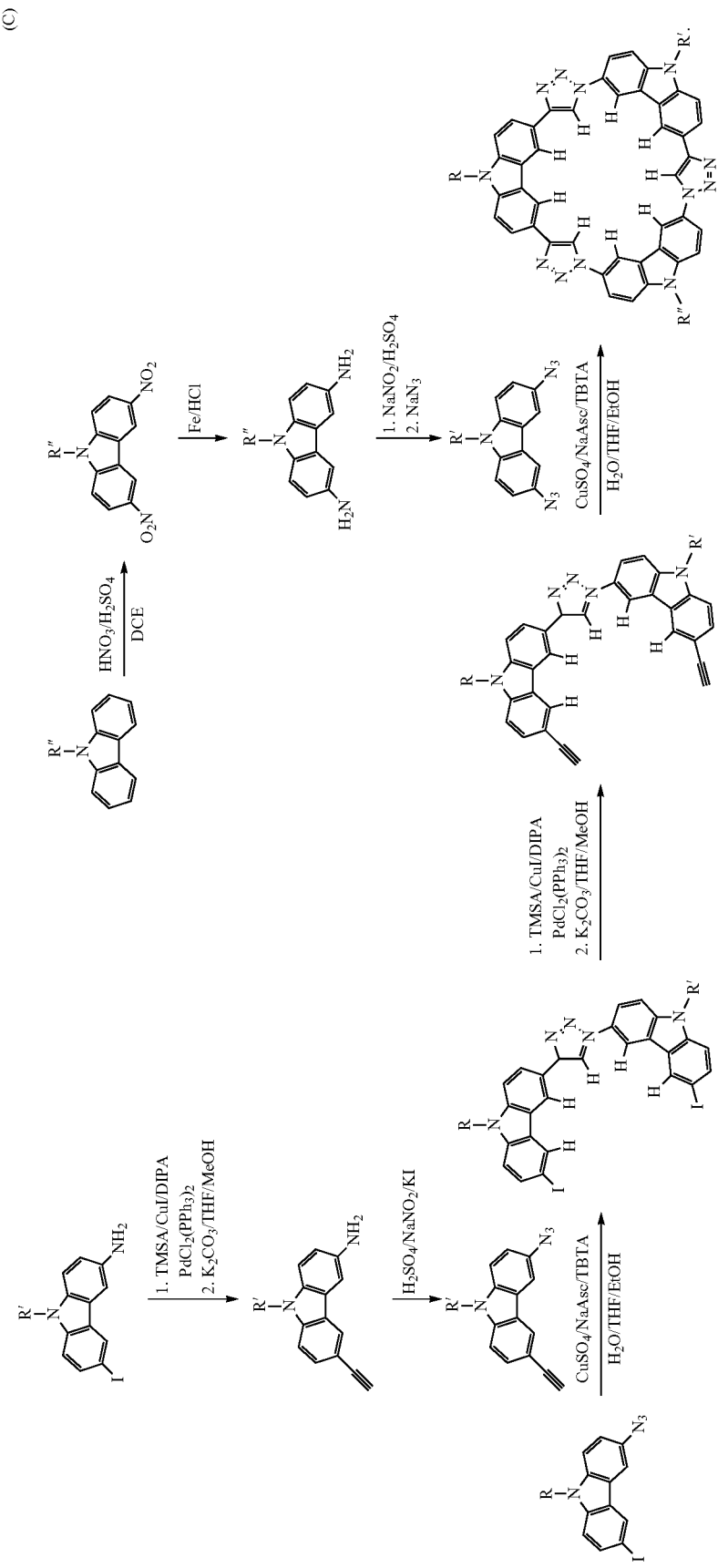

Referring to Scheme (C), starting from carbazole, nitrogen alkylation followed by sequential reactions to add azido and ethynyl groups on the 3 and 6 positions, respectively, provided a difunctional monomer with an overall 68% yield for seven steps. Cu-catalyzed cycloaddition between the azido and alkynyl groups of the aforementioned monomer under high dilution conditions (preferably, with slow addition of monomer into the reaction) resulted in tricarb of Formula (IB) with 70% yields that can be conducted on gram scales.

For the synthesis of the proof-of-principle tricarb compound (IB), synthetic Scheme (D) was used:

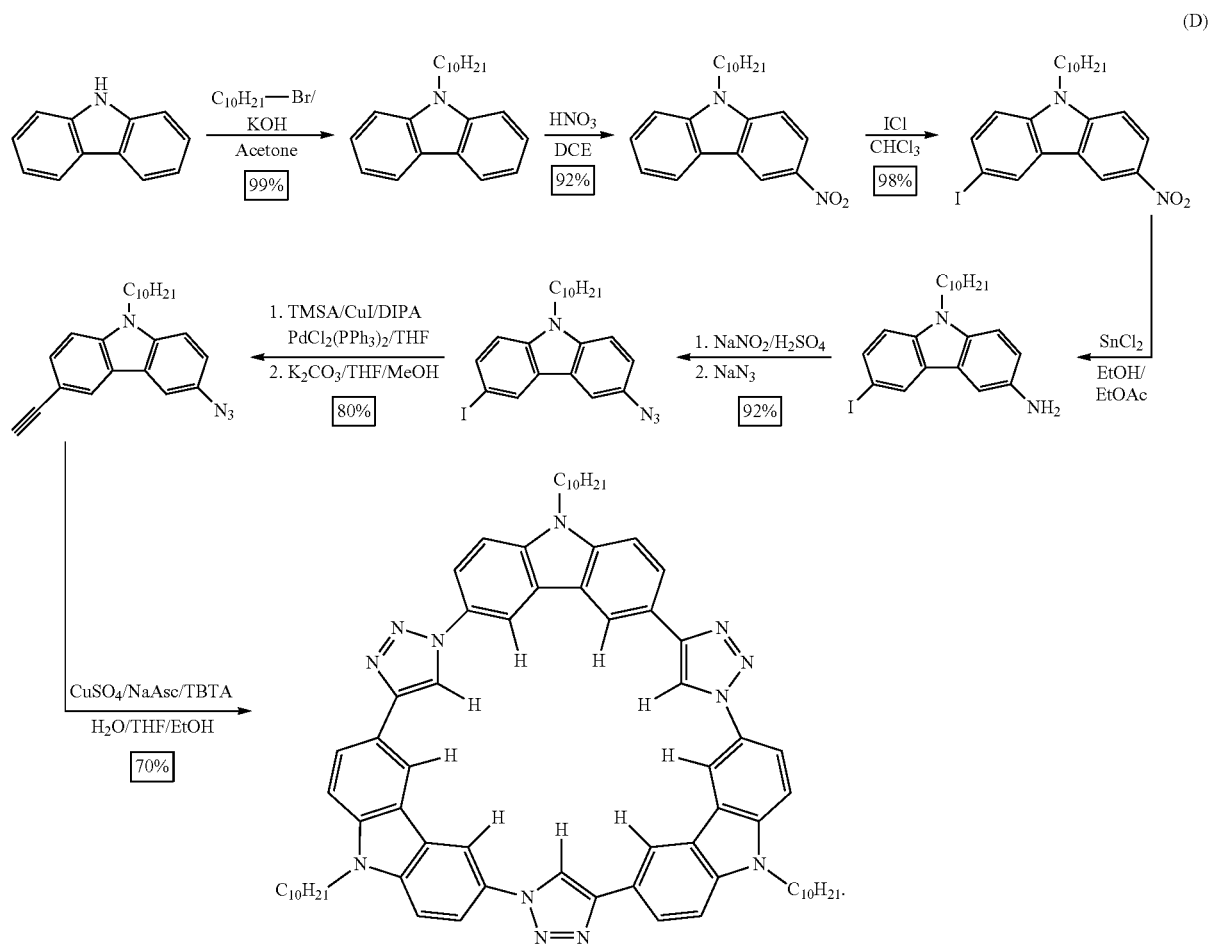

(D)

Substituents can be incorporated into the carbazole's structure of Formulas (I), (II) and (III), as illustrated for an exemplary variant embodiment of Formula (IB) made according to synthetic Scheme (E):

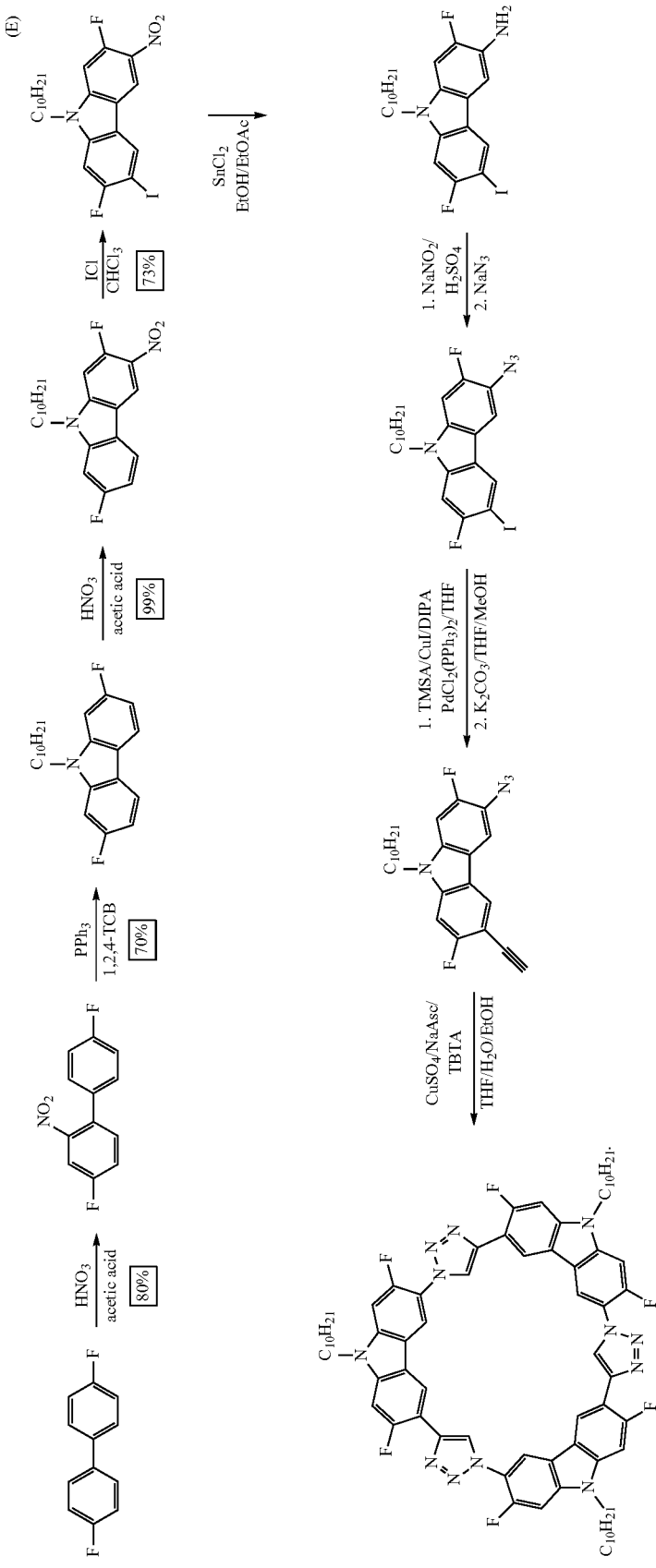

Any of the hydrogens of the carbazole moieties can be replaced by any suitable substituents, such as halogens, alkyls, CN, carboxylates, esters, alkynes, among others.

Anion Binding Properties of Tricarbs of Formulas (I), (II) and (III)

Tricarbs of Formulas (I), (II) and (III) have anion binding properties. Tricarb has an electropositive cavity (FIG. 1) lined by six carbazole and three triazole CH protons for binding anions. Tricarb has smaller ESP values (~170 kJ mol$^{-1}$) and larger cavity (d=4.8 Å) than cyanostars (S. Lee, C. H. Chen, A. H. Flood, *Nat. Chem.* 2013, 5, 704-710) (ESP ~180 kJ mol$^{-1}$, d=4.5 Å) and triazolophanes (Y. Li, A. H. Flood, *Angew. Chem. Int. Ed.* 2008, 47, 2649-2652) (ESP ~250 kJ mol$^{-1}$, d=3.7 Å). A peak selectivity for anions larger than the cyanostar's preference for $PF_6^-$ but with lowered affinities is expected for tricarb compounds having Formulas (I), (II) and (III).

Figure 2:
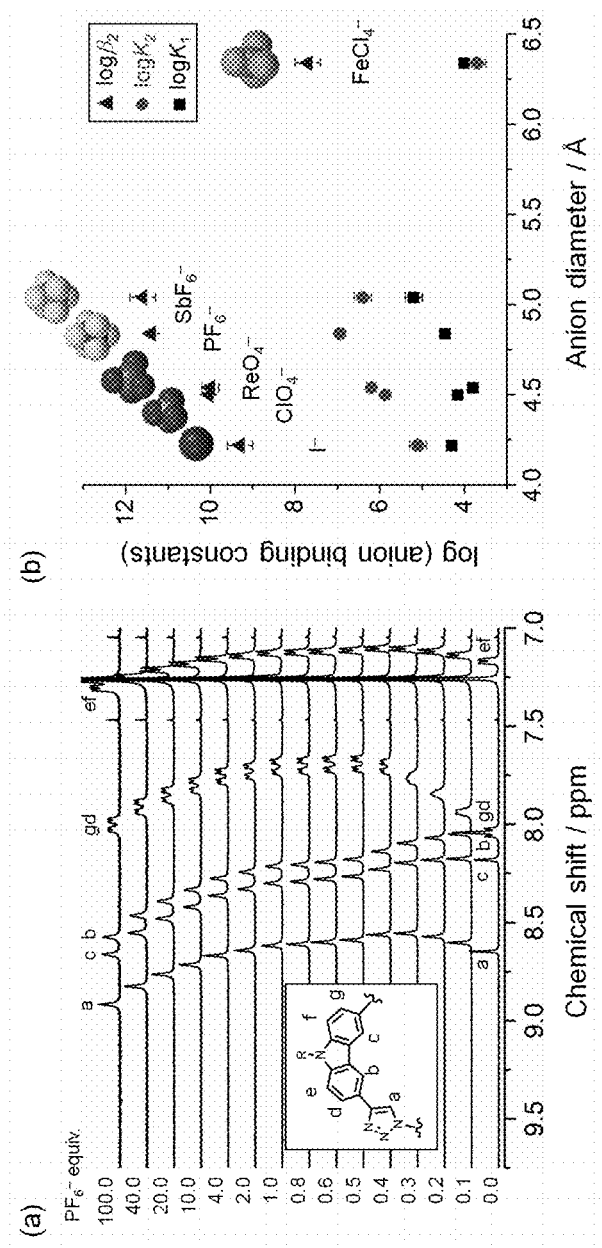
FIG. 2A depicts exemplary spectra of $^1H$ NMR titration of tricarb of Formula (IB) (1 mM) with $TBAPF_6$ (20% $CD_3OD/CDCl_3$, 500 MHz, 298 K).
FIG. 2B depicts an exemplary plot of anion binding constants obtained from equilibrium restricted factor analysis (D. A. Griend, D. K. Bediako, M. J. DeVries, N. A. DeJong, L. P. Heeringa, *Inorg Chem* 2008, 47, 656-662) of UV-Vis titration data (20% $MeOH/CHCl_3$). Salts added as $TBA^+$ with exception of $FeCl_4^-$ added as the 1-ethyl-3-methylimidazolium salt.

Anion binding titrations with tricarb were observed with $^1$H NMR spectroscopy (FIG. 2) and conducted in 20% v/v chloroform/methanol to dissociate tetrabutylammonium (TBA$^+$) salts into ions. Addition of $PF_6^-$ shows proton shifts indicative of complexation. Inner carbazole protons (H$^b$, H$^c$) shift downfield consistent with weak CH . . . anion H-bonding. The strong H-bonding triazoles (H$^a$) show up-field shifts up to ~0.5 equivalents of $PF_6^-$ followed by continuous downfield shifts (FIG. 2A). This chemical shifting pattern is consistent with prior observations (Y. Hua, R. O. Ramabhadran, E. O. Uduehi, J. A. Karty, K. Raghavachari, A. H. Flood, *Chem. Eur. J.* 2011, 17, 312-321) indicating formation of a 2:1 sandwich complex with net upfield shifts (H$^a$:π stacking>H-bonding) followed by gradual transformation into 1:1 complexes (H$^a$:H-bonding alone). The swing in the positions of the outer carbazole protons (H$^d$, H$^e$, H$^f$, H$^g$) follows the differences in π stacking.

The tricarb-anion stability constants were determined from UV-Vis titrations and evaluated using equilibrium restricted factor analysis (D. A. Griend, D. K. Bediako, M. J. DeVries, N. A. DeJong, L. P. Heeringa, *Inorg Chem* 2008, 47, 656-662) as implemented with Sivvu by employing the following equilibria:

  (1)

  (2)

  (3)

Tricarb of Formula (IB) shows peak binding for size-matched $PF_6^-$ and $SbF_6^-$ anions (FIG. 2B). Anions of various sizes ranging from I$^-$ (d~4.2 Å) to $FeCl_4^-$ (d~6.3 Å) were examined. The binding affinities of large anions are uncharacteristically large: log β$_2$ for $SbF_6^-$ (11.6), $PF_6^-$ (11.4) and $ClO_4^-$ (10). These results are surprising, in view of the long-accepted idea that the binding of large anions is weak (M. R. Rosenthal, *J. Chem. Ed.* 1973, 50, 331-335). As predicted from ESP values, overall stabilities of the 2:1 sandwiches (β$_2$) were about an order of magnitude weaker when compared to cyanostar with a preference for slightly larger anions. The positive cooperativity is higher for tricarb of Formula (I) than cyanostar ranging from K$_2$/K$_1$~5 for I$^-$ and $FeCl_4^-$ and growing through ~30 ($SbF_6^-$) and ~70 ($ClO_4^-$) to be as high as 200 for $ReO_4^-$ and 300 for $PF_6^-$. These values are commensurate with the greater planarity of tricarb of Formulas (I) and (II) over cyanostars and consistent with the dipole pairing between π (pi) faces (vide infra).

Table I summarizes anion-binding constants for tricarb of Formula (IB) for several tetrabutylammonium salts of exemplary anions.

TABLE 1

Anion binding constants (logK) of tricarb determined by UV-Vis titration of tetrabutylammonium salts, 20% MeOH/CHCl$_3$ (1-ethyl-3-methylimidazolium salt was used for $FeCl_4^-$).$^a$

| | diameter (Å) | logK$_1$ | logK$_2$ | logβ$_2$ | K$_2$/K$_1$ |
|---|---|---|---|---|---|
| I$^-$ | 4.2 | 4.3 ± 0.1 | 5.1 ± 0.2 | 9.3 ± 0.3 | 6 ± 3 |
| $ClO_4^-$ | 4.5 | 4.04 ± 0.01 | 5.87 ± 0.01 | 10.04 ± 0.02 | 67 ± 3 |
| $ReO_4^-$ | 4.54 | 3.8 ± 0.1 | 6.2 ± 0.1 | 10.0 ± 0.2 | 200 ± 100 |
| $PF_6^-$ | 4.84 | 4.46 ± 0.01 | 6.94 ± 0.01 | 11.40 ± 0.02 | 300 ± 60 |
| $SbF_6^-$ | 5.04 | 5.2 ± 0.2 | 6.4 ± 0.2 | 11.6 ± 0.4 | 30 ± 20 |
| $FeCl_4^-$ | 6.34 | 4.0 ± 0.1 | 3.7 ± 0.2 | 7.7 ± 0.3 | 5.2 ± 0.2 |

$^a$Values were obtained from equilibrium-restricted factor analyses of UV-Vis titration data across all wavelengths as implemented with Sivvu (D. A. Vander Griend, D. K. Bediako, M. J. DeVries, N. A. Belong, L. P. Heeringa, *Inorg. Chem.* 2007, 47, 656-662). The errors were determined by re-optimizing the binding constants 40 times with 50% of the wavelengths randomly excluded.

In preferred embodiments, the ratio of tricarb of Formulas (I), (II) or (III) to anion in the formed complexes can be any ratio. These can be selected from the following list but are not limited to this selection: 1:1 (tricarb:anion), 2:1 (tricarb:anion), 2:2 (tricarb:anion) and 3:2 (tricarb:anion). Mixtures of tricarbs of Formulas (I), (II) and (III) can be included in complexes formed with anions.

Tricarbs of Formulas (I), (II) and (III) Form Thin Films

Figure 3:
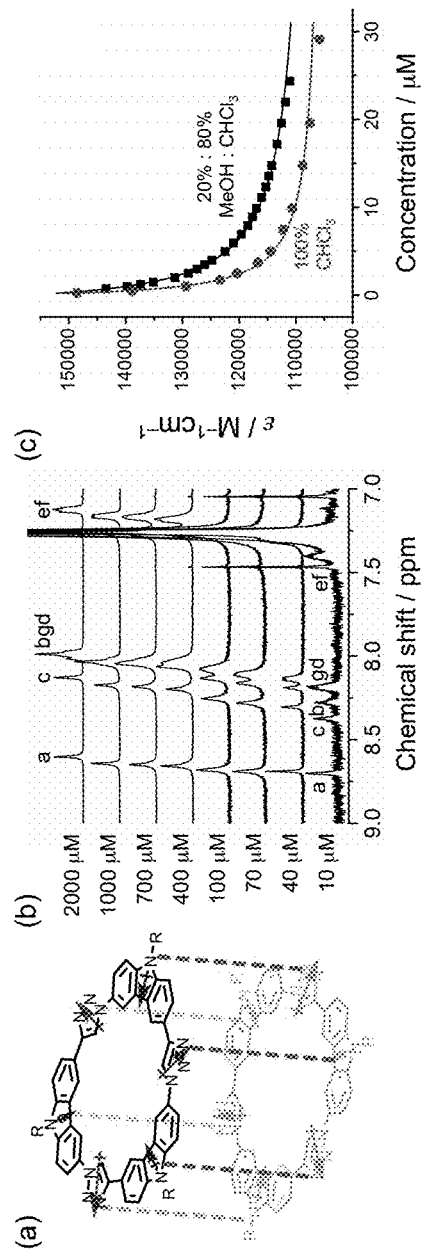
FIG. 3A depicts a proposed mode of dipole-aligned stacking of tricarb of Formula (IB).
FIG. 3B depicts exemplary variable concentration $^1H$ NMR spectra of tricarb of Formula (IB) (20% $CD_3OD/CDCl_3$, 500 MHz, 298 K).
FIG. 3C depicts exemplary variable concentration plots of UV-Vis extinction maxima (20% $MeOH/CHCl_3$ and $CHCl_3$).

The multifunctional character of the tricarbs of Formulas (I), (II) and (III) emerges in their propensity to self-associate. A variety of factors are believed to enable stacking-based self-association. For example, molecular modeling (B3LYP/6-31G*) shows tricarb of Formula (I) is an approximately flat macrocycle (FIG. 1) with a wagon-wheel of alternating dipole moments from the carbazoles and triazoles. Stacking thus enables formation of dipolar contacts (FIG. 3A) with an expected intermolecule rotation of ~60.

Solution phase self-association was examined using variable concentration $^1$H NMR and UV-Vis spectra. All aromatic $^1$H NMR peaks shift upfield (FIG. 3B) with concentration (10×10$^{-6}$ M–2×10$^{-3}$ M) consistent with p stacking (R. B. Martin, *Chem. Rev.* 1996, 96, 3043-3064). UV-Vis spectroscopy was used to quantify the extent of self-association (S. A. Jenekhe, L. Lu, M. M. Alam, *Macromolecules* 2001, 34, 7315-7324) (0.7 to 24×10$^{-6}$ M, FIG. 3C). An isodesmic equal-K model (R. B. Martin, *Chem. Rev.* 1996, 96, 3043-3064) was used to quantify self-association (K$_E$) to give K$_E$=300,000±10,000 M$^{-1}$ in 20% MeOH/CHCl$_3$ (ε=10.4). The self-association is high relative to other macrocycles (W. Zhang, J. S. Moore, *Angew. Chem. Int. Ed.* 2006, 45, 4416-4439) and believed to be driven by solvophobic effects and dipolar coupling. Consistent with dipolar coupling, use of pure CHCl$_3$ with a lower polarity (ε=4.8), increases K$_E$ to 790,000±30,000 M$^{-1}$ (S.-L. Lee, Z. Yuan, L. Chen, K. S. Mali, K. Müllen, S. De Feyter, *J Am. Chem. Soc.* 2014, 136, 4117-4120; S.-L. Lee, Z. Yuan, L. Chen, K. S. Mali, K. Müllen, S. De Feyter, *J. Am. Chem. Soc.* 2014; P. Samori, N. Severin, C. D. Simpson, K. Müllen, J. P. Rabe, *J. Am. Chem. Soc.* 2002, 124, 9454-9457).

The self-association was also found to exist at the liquid-solid interface, where highly ordered arrays of 2D crystalline monolayers were found to grow into multilayers by the stacking of a faces. Deposition of a 1,2,4-trichlorobenzene (TCB) droplet of a solution of tricarb of Formula (IB) onto a freshly cleaved surface of highly oriented pyrolytic graphite (HOPG) and subsequent STM imaging (FIG. 4) revealed two polymorphs. A low-density flower structure (FIG. 4A) with separated rosettes coexists with a densely packed honeycomb with fused rosettes (FIG. 4C) at 75×10$^{-6}$ M, while at 150×10⁻⁶ M the honeycomb is favored. The corresponding packing structure of each polymorph (FIGS. 4D and 4F) was determined from high-resolution STM images and aided by modeling of lateral H-bonding (ESI).

Tricarb-tricarb contacts are believed to be identical in the flower and honeycomb polymorphs. Tricarbs appear with bright contrast and make intimate contact with neighbors in the rosettes (two neighbors for the flower and three in the honeycomb). The macrocycle cores are believed to form lateral H-bonding contacts between carbazole CH donors (D) and triazole N-atom acceptors (A) (FIG. 4E, green), constituting a DDAA array (J. R. Quinn, S. C. Zimmerman, J. E. Del Bene, I. Shavitt, *J. Am. Chem. Soc.* 2007, 129, 934-941; S. E. Wheeler, J. W. G. Bloom, *J. Phys. Chem. A* 2014, 118, 6133-6147.) between edges of each triangular tricarb.

The flower polymorph is believed to form a co-crystal with the TCB solvent as evidenced from three features seen in the STM images; FIG. 4A, black box. Multiple CH . . . Cl contacts between carbazole and TCB are proposed allowing the solvent to act as a molecular "mortar" (M. O. Blunt, J. Adisoejoso, K. Tahara, K. Katayama, M. Van der Auweraer, Y. Tobe, S. De Feyter, *J. Am. Chem. Soc.* 2013; C. Marie, F. Silly, L. Tortech, K. Müllen, D. Fichou, *ACS Nano* 2010, 4, 1288-1292; A. Langner, S. L. Tait, N. Lin, R. Chandrasekar, M. Ruben, K. Kern, *Chem. Commun.* 2009, 2502-2504) between the bricks of tricarb rosettes (FIG. 4D, inset). Without the claimed subject matter being limited in any way, this packing model (FIG. 4E) represents the most plausible structural configuration.

The packing of tricarb depends on its lateral nearest-neighbor interactions. Tricarb is prochiral and can adsorb with either R or S configuration (assigned from triazole units, FIG. 4E). There are three plausible H-bond DDAA patterns between tricarb neighbors, depending on R/S orientation and position of the triazoles. The most stable array occurs between pairs of either RR or SS (FIG. 4E) macrocycles. Other configurations, a different homochiral pairing and a heterochiral contact (RS), are less favored. Modeling suggests the homochiral contact in FIG. 4E is most stable. This orientation also provides the best pairing of triazole dipoles (red dipoles, FIG. 4E). Propagation of these contacts to all nearest neighbors suggests all rosettes and fused rosettes form homochiral conglomerates. Consistently, twinned domains of the honeycomb are observed. The unit cells of each twin are +200 (P rosettes of S enantiomers) and −20° (M rosettes of R) from the main symmetry axis of graphite. Conveniently, the apices of the triangular tricarb macrocycles inside the rosette pores point clockwise (P, FIG. 4F) or counter-clockwise (M). The flower and honeycomb polymorphs share unit cell directions suggesting both form conglomerates. Chiral information is believed to be transmitted between molecules through edge-sharing contacts that establish handedness in the rosettes and bias domains towards conglomerates.

Figure 4:
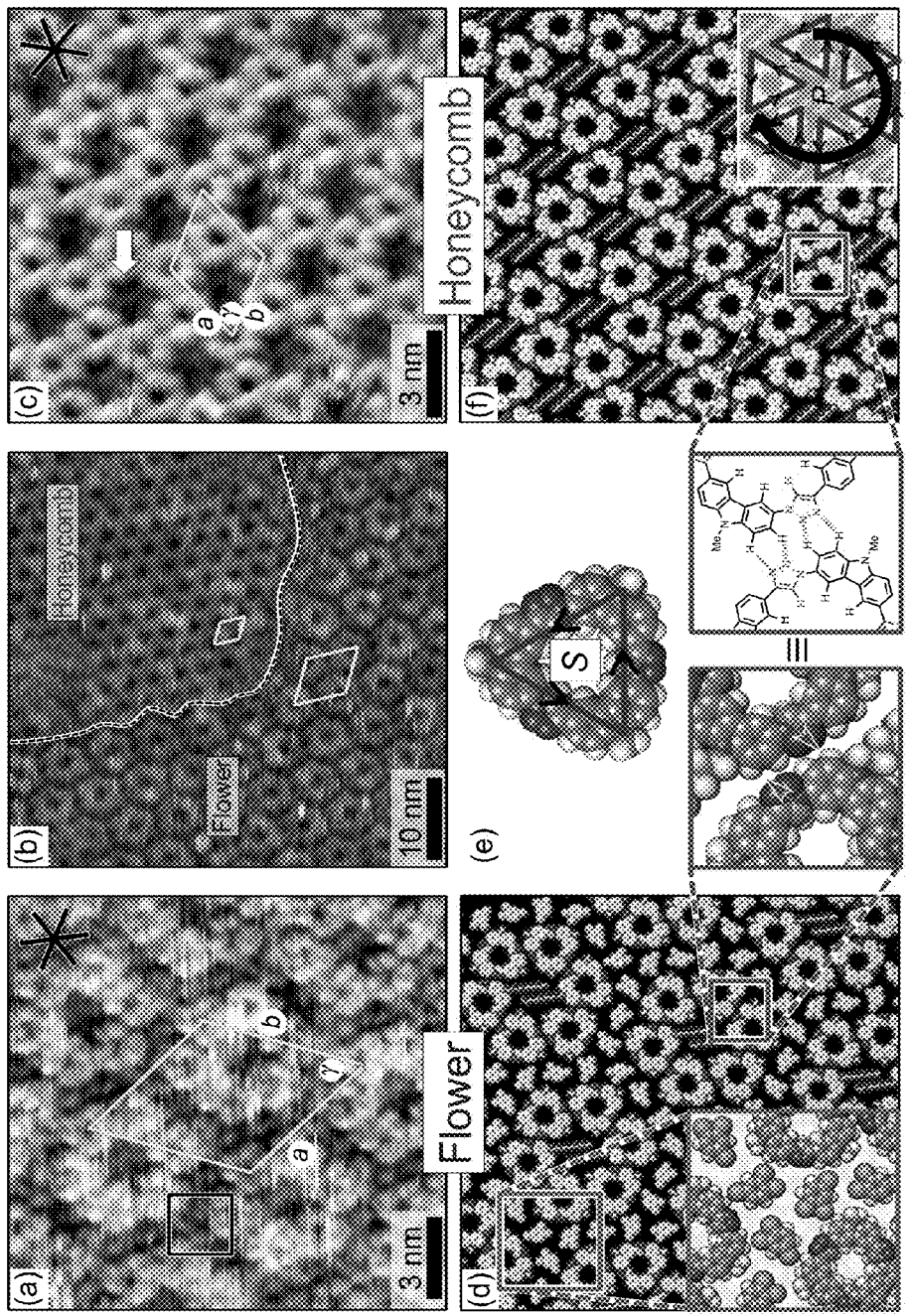
FIG. 4A depicts exemplary high-resolution STM images and packing models of tricarb at TCB/graphite interface, wherein the flower structure with separated "rosettes" consisting of six tricarb molecules (a=b=5.34±0.11 nm, γ=60±1°). Conditions: 75×$10^{-6}$ M, $I_T$=30 pA, $V_{sample}$=−0.3 V.
FIG. 4B depicts an exemplary honeycomb structure, with a hexagonal, fused nanopore network (a=b=2.89±0.09 nm, γ=60±1°). Conditions: 75×$10^{-6}$ M, $I_T$=30 pA, $V_{sample}$=−0.3 V.
FIG. 4C depicts an exemplary STM image showing coexistence, shared unit cell vector directions and density differences of flower and honeycomb polymorphs. Conditions.
FIG. 4D depicts proposed packing model for the flower polymorph.
FIG. 4E depicts proposed packing model showing P chirality of a rosette composed of S enantiomers of tricarb (top) and a detailed view of DDAA seam (bottom).
FIG. 4F depicts proposed packing model for the honeycomb polymorph (inset).

High-resolution STM images of the honeycomb clearly resolve the central cavity of the donut-shaped macrocycles (FIG. 4A). Each macrocycle bears bright features assigned to carbazoles that match with rotation angles in the packing models (FIG. 4). Low contrast features observed within rosette pores are assigned to adsorption of two $C_{10}$ chains. The other four chains are not observed and believed to fold into the solution (C. Marie, F. Silly, L. Tortech, K. Müllen, D. Fichou, *ACS Nano* 2010, 4, 1288-1292; W. Mamdouh, H. Uji-i, J. S. Ladislaw, A. E. Dulcey, V. Percec, F. C. De Schryver, S. De Feyter, *J. Am. Chem. Soc.* 2005, 128, 317-325). While decyl chains of tricarb of Formula (IB) were introduced to direct surface assembly, the H-bonded seams between macrocycles clearly dominate lateral ordering.

The observation of multiple-layer adsorption events as indicated by the many higher contrast molecules seen in the STM images is surprising (FIG. 5A). Interestingly, multilayers are also seen on the low-density flower polymorph (75×10⁻⁶ M, FIG. 4B); an observation consistent with the high self-association of tricarb. Doubling the concentration promotes the honeycomb and significantly favors co-facial stacking (FIG. 5A). Consistent with prior works showing STM imaging of bilayers, multilayers are seen with a reduced tunneling set-point (L. Piot, C. Marie, X. Feng, K. Müllen, D. Fichou, *Adv. Mater.* 2008, 20, 3854-3858).

Five distinct levels of height contrast (FIG. 5A, colored boxes) are observed in STM analyses. Comparison of line profiles to monolayer images allow the assignment of these levels to co-facial stacking of tricarb macrocycles into tubes up to five molecules tall. The stacking maintains registry with the monolayer; no differences were observed in the unit cells between monolayer and multilayer (FIG. 5A insert, and S40). Remarkably, the central tricarb cavity is still resolved in line profiles (FIG. 5B and ESI). The apparent height difference between layers in the STM images (~0.8 Å) is lower than ~3.4 Å for π stacks but consistent with prior imaging (D. Skomski, J. Jo, C. D. Tempas, S. Kim, D. Lee, S. L. Tait, *Langmuir* 2014, 30, 10050-10056). Thus, the tallest stacks constitute tubes running ~1.7 nm in height. The observed high degree of vertical ordering is rare and likely represents interfacial encoding of the planar surfaces of macrocycle.

Dipole stabilization and steric contacts are believed to act as molecular alignment markers guiding inter-layer registration. Modeling favors 60° (anti-parallel dipoles) rotations between stacked macrocycles. However, 3D model show that 60° rotations produce steric clashes between lateral neighbors arising from carbazolo apices. Refinement of the packing indicates 32° allow tricarb molecules in the second layer to make the same DDAA H-bonding seen in the first layer. These same DDAA contacts require the configuration of the tricarb to be flipped e.g., S to R. Consequently, molecular and rosette chirality is believed to alternate between layers. The 32° rotation is not observed by STM imaging, rather it emerges as a likely 3D packing arrangement after model refinement. The final structural model (FIG. 4C) shows the S macrocycles arranged into P rosettes in one layer alternating with R macrocycles in M rosettes in the next layer to produce ABAB ordering in the third dimension. Thus, the vertical alignment of macrocycles is believed to be directed by the steric restraints placed on dipole alignments, and the optimization of lateral edge-sharing contacts to produce a inversion of molecular and rosette chirality between layers.

The multilayer structure does not grow indefinitely. At 150 μM, the stacking distribution is: single molecules (32%), dimers (40%), trimers (24%) and four, five or more molecules (2%). Furthermore, the multilayer does not appear to follow layer-by-layer growth; rather the heights frequently differ between neighboring sites (S. Lee, C. H. Chen, A. H. Flood, *Nat. Chem.* 2013, 5, 704-710). The maximum number of molecules around a single rosette was observed to be 19. This number is consistent with a model of the rosettes (inset, FIG. 5C) showing that the over-filling of rosette pores by decyl chains may act to limit vertical growth.

Thus, another aspect of the present invention includes tricarbazole triazolophane (tricarb) of Formulas (I), (II) and (III) having the ability to bind an anion and methods directed to anion binding and removal from mixtures. Preferred anions include at anions selected from a group consisting of I$^-$, ClO$_4^-$, ReO$_4^-$, PF$_6^-$, SbF$_6^-$, FeCl$_4^-$, mesylate (CH$_3$SO$_3^-$), triflate (CF$_3$SO$_3^-$), arsenate (AsO$_4^{3-}$), hexafluoroarsenate (AsF$_6^-$), tetrachloroaluminate (AlCl$_4^-$), phosphate (PO$_4^{3-}$), hydrogenophosphate (HPO$_4^{2-}$), dihydrogenophosphate (H$_2$PO$_4^-$), sulfate (SO$_4^{2-}$), hydrogen sulfate (HSO$_4^-$), tetracyanoborate (B(CN)$_4^-$), halides (Cl$^-$, Br$^-$, I$^-$), cyanide, perbromate (BrO$_4^-$), periodate (IO$_4^-$), fluoride (F$^-$), bifluoride (HF$_2^-$), pertechnetate (TcO$_4^-$), monosubstituted phosphate esters (RPO$_4^{2-}$), disubstituted phosphate esters (R$_2$PO$_4^-$), organosulfonates (RSO$_3^-$), thiocyanate, (SCN$^-$), azide (N$_3^-$), triiodide (I$_3^-$), carbonate (CO$_3^{2-}$), monohydrogen carbonate (HCO$_3^-$), iron tetrachlorate (FeCl$_4^-$), gold dicyanate (Au(CN)$_2^-$), acetate (CH$_3$CO$_2^-$), uranium hexafluoride (UF$_6^-$), sulfide (S$^{2-}$), and platinum hexachlorate (PtCl$_6^{2-}$), among others, or a combination thereof, including mono- and poly-protonated forms (e.g., AsO$_4^{3-}$, HAsO$_4^{2-}$ and H$_2$AsO$_4^-$). In addition to the anions listed above, anions selected from tables in the following paper will also be viable: "Thermochemical Radii of Complex Ions" *J. Chem. Ed.* 1999, 76, 1570-1573, which is incorporated herein by reference in its entirety. Preferred anions from this reference that would bind to a composition of tricarbs selected from Formulas (I), (II) and (III), or a combination thereof, include those having a thermochemical radius between 0.16 Å and 0.33 Å. In addition to these anions, the following polysulfides anions are highly preferred: S$_2^{2-}$, S$_4^{2-}$, S$_6^{2-}$, S$_8^{2-}$ and S$_n^{2-}$, where n is an even number. The anions that can serve as suitable candidates for binding the composition of tricarbs selected from Formulas (I), (II) and (III), or a combination thereof, include any isolated or combination of anions from the above disclosed listing.

In this regard, a method of binding an anion is contemplated. The method includes a step of contacting the anion with a tricarbazole triazolophane (tricarb) of Formulas (I), (II) and (III), or a combination thereof, as described herein. Likewise, a method of removing an anion from a mixture is also contemplated. The method includes two steps. The first step includes contacting the mixture with a tricarbazole triazolophane (tricarb) of Formulas (I), (II) and (III), or a combination thereof, as described herein to form a complex of an anion and tricarb of Formulas (I), (II) and (III), or a combination thereof. The second step includes separating the complex from the mixture.

Figure 6:
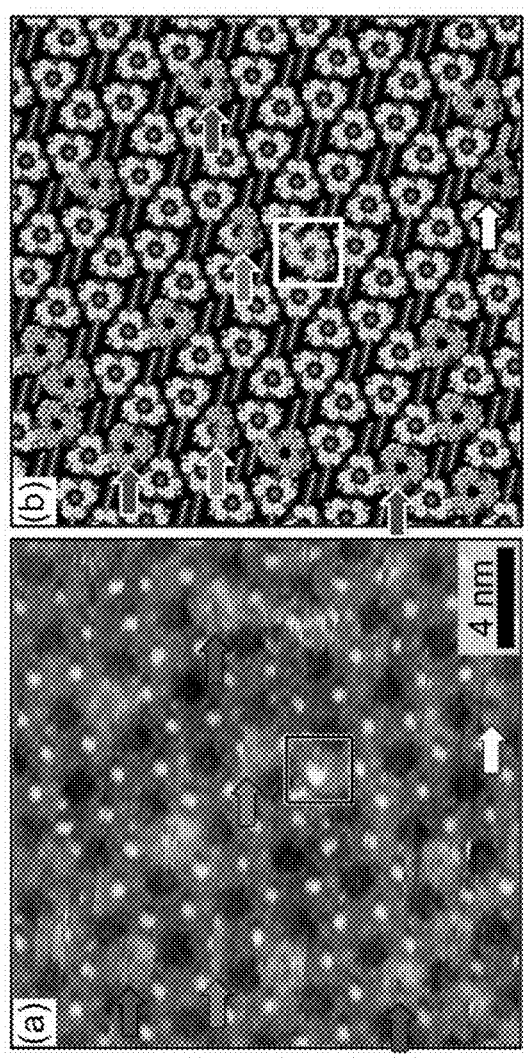
FIG. 6A depicts an exemplary STM image of tricarb of Formula (IB) in the honeycomb structure with 0.005 eq. of TBAI added at the TCB/graphite interface. Bright circular features located at the centers of macrocycles are assigned to bound I$^-$. Green molecules indicate unbound multilayer sites. Purple molecules highlight dynamic movement of I$^-$ anions between scan lines allowing formation of a multilayer stack. The white box (yellow molecule) likely shows a 2:1 sandwich complex, and the white arrow (orange molecule) points to an unbound monolayer tricarb site. Conditions: [tricarb]=150×10$^{-6}$ M, $I_T$=81 pA, $V_{sample}$=−0.44 V.
FIG. 6B depicts a model of tricarb of Formula (IB) in the honeycomb structure with 0.005 eq. of TBAI added at the TCB/graphite interface as in FIG. 6A. Bright circular features located at the centers of macrocycles are assigned to bound I$^-$. Green molecules indicate unbound multilayer sites. Purple molecules highlight dynamic movement of I$^-$ anions between scan lines allowing formation of a multilayer stack. The white box (yellow molecule) likely shows a 2:1 sandwich complex, and the white arrow (orange molecule) points to an unbound monolayer tricarb site. [tricarb]=150×10$^{-6}$ M, $I_T$=81 pA, $V_{sample}$=−0.44 V.

Contact between the anion and the tricarb selected from Formulas (I), (II) and (III), or a combination thereof, can be made in any state of matter: solid, liquid or gas. The liquid could be any solution bearing the anion and any solution bearing the tricarb. The solutions could be made from any known liquid, such as, methanol and dichloromethane mixture (FIG. 3B), a methanol-chloroform mixture (FIG. 3C), chloroform (FIG. 3C), trichlorobenzene (FIGS. 4A and 6A). All other liquids in which the anion is soluble, including, water, glycols, alcohols, ketones, sulfoxides, ethers, halogenated liquids, alkanes, carboxylic acids, and amides.

Anion Binding to Thin Films Comprising Tricarbs of Formula (I), (II) and (III)

The ability of the cavity of the tricarb macrocycle to bind anions at the liquid-solid interface was also investigated. Remarkably, in-situ addition of only 0.005 eq of iodide relative to the total number of molecules in solution showed bright features located in the central cavity of each tricarb macrocycle (FIG. 6A). Not every site is occupied, thus excluding the possibility of inverted contrast from changes in the density of electronic states of the tip. Occasionally, in-and-out dynamics of anions (FIG. 6A, purple arrows) can be observed, a result we have seen previously (B. E. Hirsch, K. P. McDonald, B. Qiao, A. H. Flood, S. L. Tait, *ACS Nano* 2014, 8, 10858-10869; B. E. Hirsch, S. Lee, B. Qiao, C.-H. Chen, K. P. McDonald, S. L. Tait, A. H. Flood, *Chem. Commun.* 2014, 50, 9827-9830; J. W. Colson, A. R. Woll, A. Mukherjee, M. P. Levendorf, E. L. Spitler, V. B. Shields, M. G. Spencer, J. Park, W. R. Dichtel, *Science* 2011, 332, 228-231). Similarly, the self-association of the tricarb molecules shows dynamic behavior.

Figure 7:
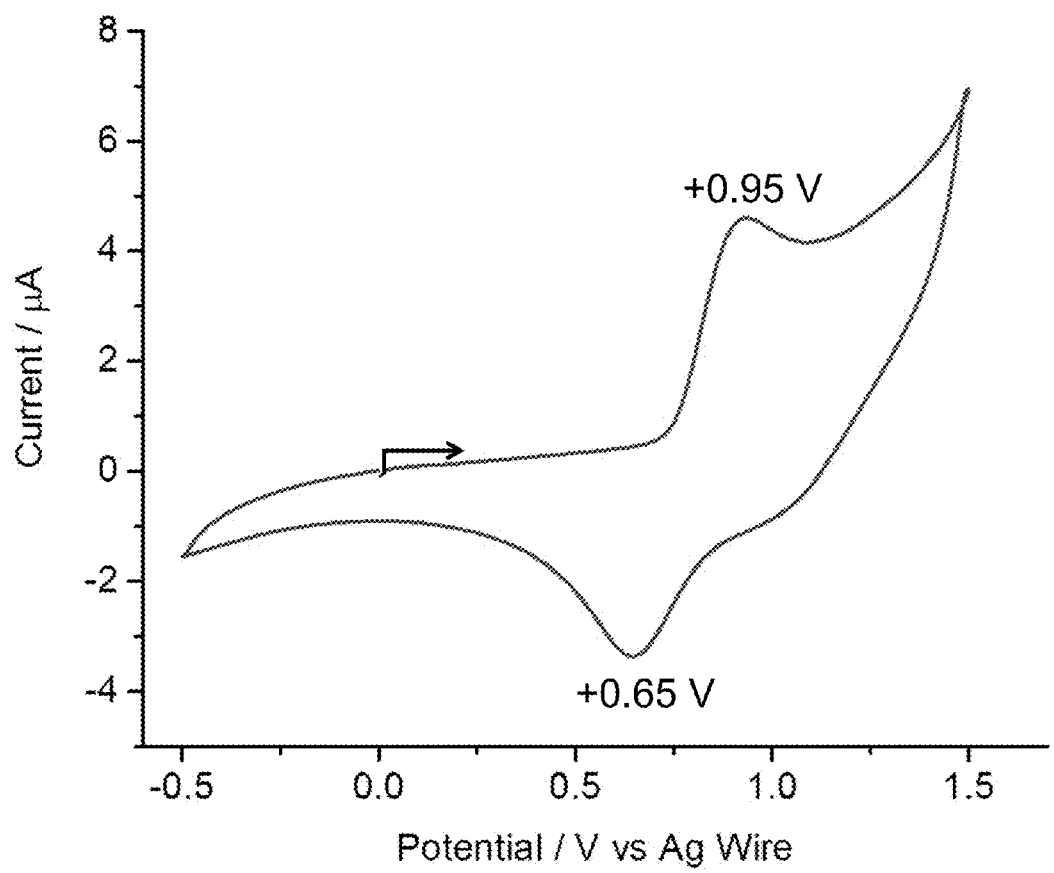
FIG. 7 depicts a representative current-voltage response curve recorded using cyclic voltammetry of tricarb of Formula (IB) in solution. The tricarb macrocycle displays peak potentials at 0.95 V and 0.65 V to define a half-wave oxidation potential of 0.8 V vs Ag/AgCl. Conditions: [tricarb of Formula (IB)]=1×10$^{-3}$ M, 0.1 M tetrabutylammonium hexafluorophosphate, glassy carbon working electrode, platinum counter electrode, chloroform, room temperature, Ar degassed.

Interestingly, the few tricarb sites that are assigned to be unoccupied by anions (FIG. 6A, green arrows) show a relative height of 0.5-1 Å consistent with tricarb dimers. Only one of the monolayer sites (orange, FIG. 6B) is missing an anion. These observations indicate anion binding promotes loss of the multilayers. This observation is consistent with the solution phase experiments (vide supra). Consequently, the anion-binding character encoded into the inner space of the macrocycles provides a way to modulate the assembly of tricarb macrocycles. The tricarb macrocycle of Formula (IB) can be readily oxidized at $E_{1/2}$=0.8 V vs Ag/AgCl (FIG. 7). This oxidation potential is consistent with the redox chemistry of the parent carbazole.

Figure 5:
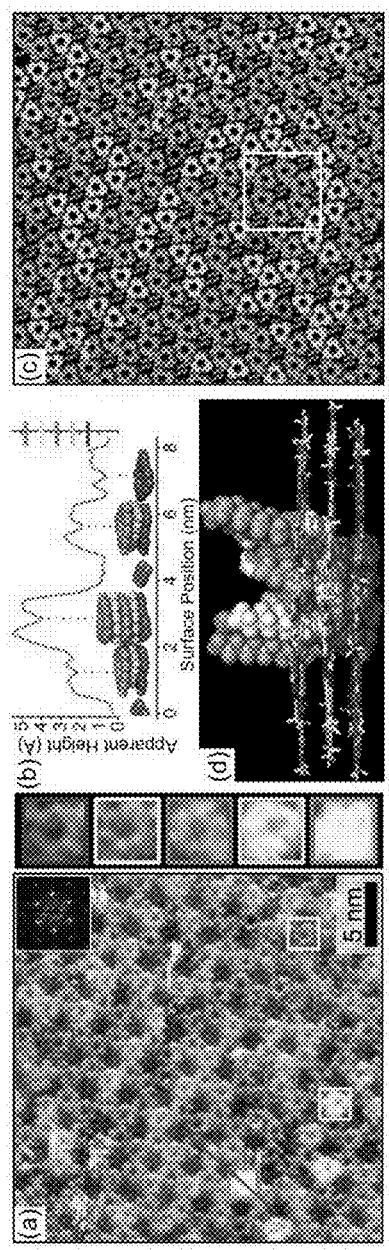
FIG. 5A depicts an exemplary high-resolution STM image of the tricarb honeycomb multilayer with five distinct levels of contrast ([tricarb]=150×$10^{-6}$ M, $I_T$=10 pA, $V_{sample}$=−0.3 V).
FIG. 5B depicts line profiles taken from image of FIG. 5A showing the discrete levels of stacking with side view of molecular models for monolayer (gray, 1.5 Å), bilayer (white, 2.25 Å), trimer (pink, 3.0 Å), tetramer (yellow, 3.75 Å) and pentamer (green, 4.5-5.0 Å). Alkyls within rosette pores are gray.
FIG. 5C depicts an exemplary top view of 3D schematic model of tubular packing of tricarb with matched color-coding.
FIG. 5D depicts an exemplary 3D molecular model side view of the densely packed rosette highlighted by a white box in FIG. 5D, where the alkyls (space filling) are shown to occupy the rosette pore.
Figure 8:
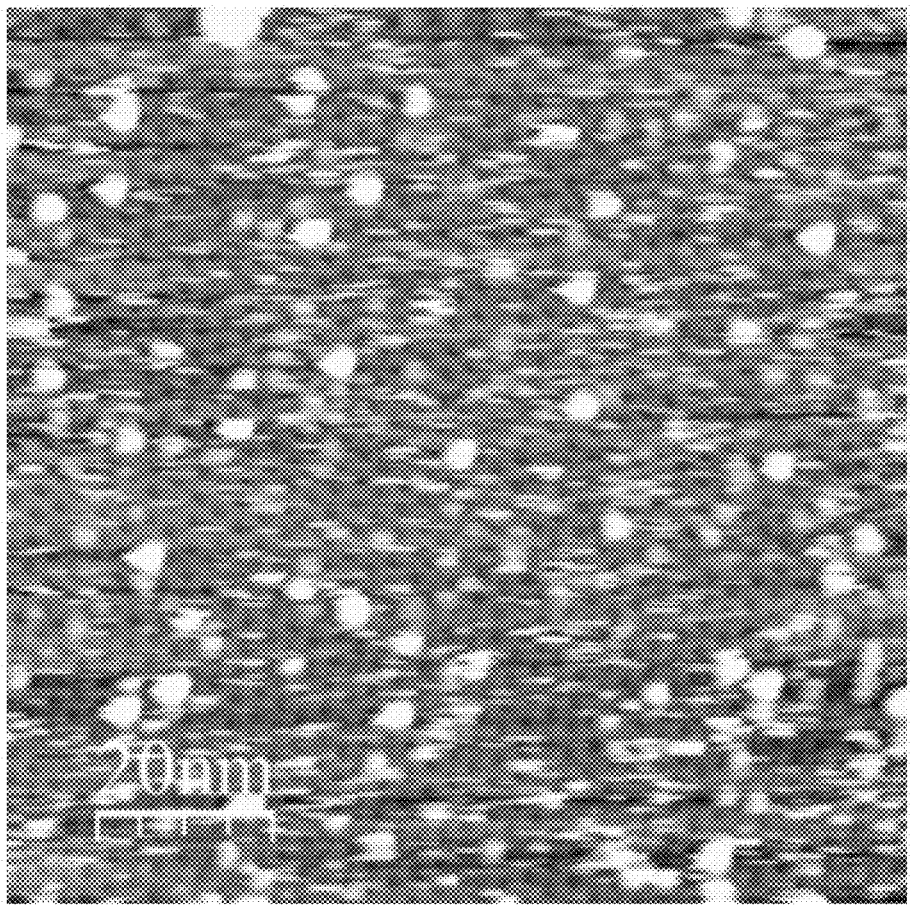
FIG. 8 depicts an exemplary STM image of tricarb of Formula (IC) in a honeycomb structure. The height contrast is consistent with the tricarb molecules of Formula (IC) forming a monolayer. The concentration of the tricarb of Formula (IC) is 200×10$^{-6}$ M.

The thickness of the multilayer comprising tricarbs of Formulas (I), (II) and (III), or a combination thereof, can be controlled by a number of physical and chemical parameters. At lower concentrations we see monolayers, e.g., at 75×10$^{-6}$ M as shown in FIG. 4C. Increasing the concentration produces multilayers, e.g., at 150×10$^{-6}$ M (FIG. 5). We showed that the addition of anions modulated the assembly of tricarb to make the layers thinner, e.g., as in FIG. 6A. In addition, the substituent can be changed to alter the stacking. For example, using a longer C$_{18}$H$_{37}$ alkyl chain in tricarb of Formula (IC) in place of the tricarb with a shorter C$_{10}$H$_{21}$ chain in tricarb of Formula (IB) leads to production of monolayers (FIG. 8) even when examined at a slightly higher concentration of 200×10$^{-6}$ M.

EXAMPLES

The invention will be more fully understood upon consideration of the following non-limiting examples, which are offered for purposes of illustration, not limitation.

Example 1. General Synthetic Methods

All reagents were obtained from commercial suppliers and used as received unless otherwise noted. 3-Amino-9-decyl-6-iodocarbazole (compound 5 of Scheme (C)) was prepared from carbazole using synthetic procedures modified from a reported preparation of 3-amino-9-hexadecyl-6-iodocarbazole (K. D. Okochi, G. S. Han, I. M. Aldridge, Y. Liu, W. Zhang, *Org. Lett.* 2013, 15, 4296-4299). Column chromatography was performed on silica gel (160-200 mesh, Sorbtech), and thin-layer chromatography (TLC) was performed on pre-coated silica gel plates (0.25 mm thick, Silicycle) and observed under UV light. Nuclear magnetic resonance (NMR) spectra were recorded on Varian Inova (400 MHz and 500 MHz) and Varian VXR (400 MHz) at room temperature (298 K). High resolution electrospray ionization (ESI) and chemical ionization (CI) mass spectrometry was performed on a Thermo Electron Corporation MAT 95XP-Trap mass spectrometer.

Example 2. Synthesis of a Tricarb of Formula (IB)

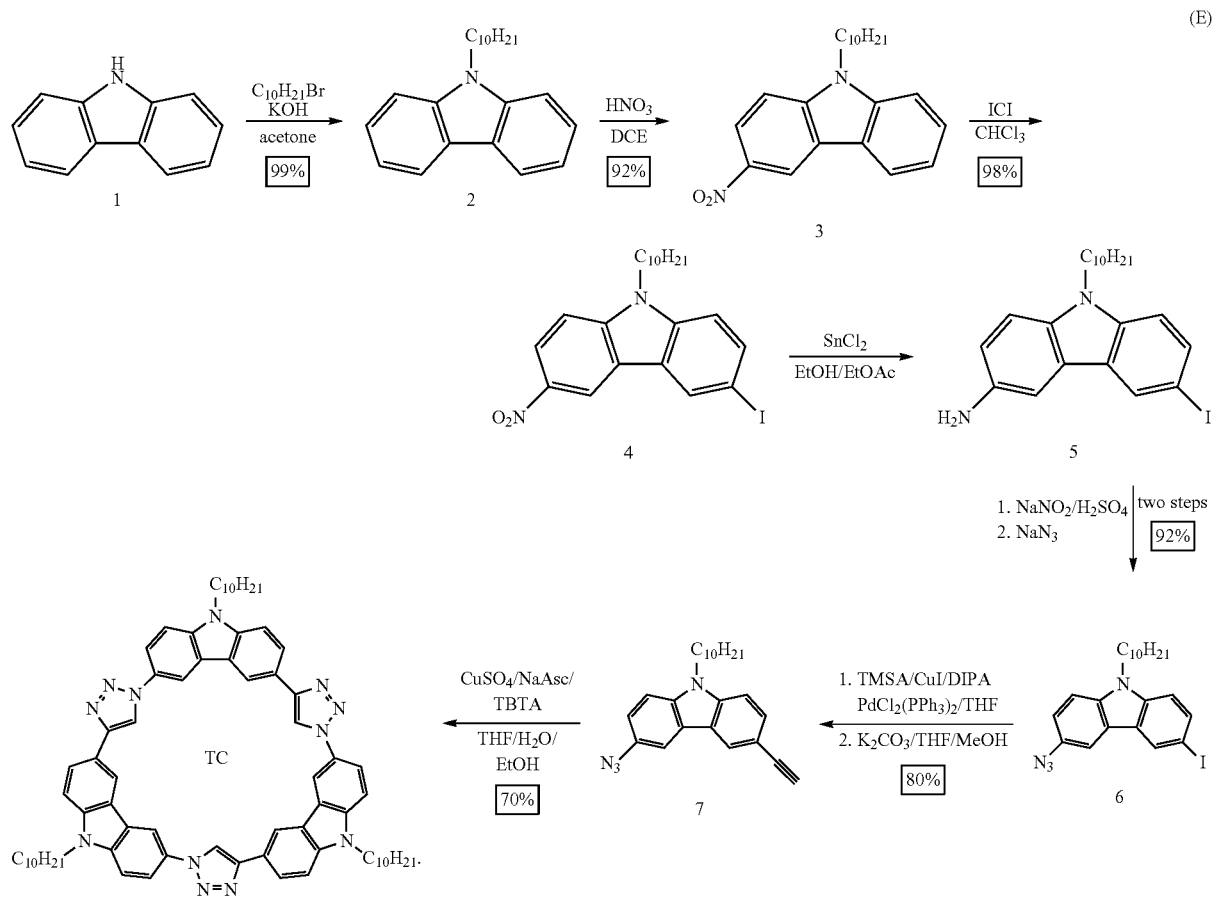

(E)

Synthesis of 9-Decylcarbazole (compound 2 of Scheme (E)): A mixture of carbazole (8.1 g, 48.4 mmol), 1-bromodecane (12.9 g, 58.1 mmol) and KOH (4.1 g, 73 mmol) in acetone (200 mL) was refluxed overnight under nitrogen atmosphere. After removing the solvent in vacuo, the mixture was extracted with EtOAc and washed with water. Column chromatography on silica gel using hexanes resulted in a colorless viscous oil product (14.8 g, 48.1 mmol, 99% yield). The $^1$H NMR spectrum was identical to previous reports (A. D. Finke, D. E. Gross, A. Han, J. S. Moore, J. Am. Chem. Soc. 2011, 133, 14063-14070).

Synthesis of 9-Decyl-3-nitrocarbazole (compound 3 of Scheme (E)): To a solution of 9-decylcarbazole (10 g, 32.5 mmol) in 1,2,-dichloroethane (100 mL) was drop-wise added nitric acid (16 M, 2.3 mL, 36 mmol) under ice bath. The reaction was heated to 60° C. and stirred for 3 h. After cooling to room temperature, water was added and the mixture was extracted with $CH_2Cl_2$. The organic layer was dried with $MgSO_4$, filtered and the solvents were removed in vacuo. The crude solid mixture was recrystallized with hexanes to result in an orange solid product (10.5 g, 29.8 mmol, 92% yield). $^1$H NMR (400 MHz, CDCl$_3$) δ=9.03 (d, J=1.6 Hz, 1H), 8.39 (dd, J=9.0, 1.6 Hz, 1H), 8.16 (d, J=7.8 Hz, 1H), 7.57 (t, J=7.8 Hz, 1H), 7.48 (d, J=8.2 Hz, 1H), 7.41 (d, J=9.0 Hz, 1H), 7.35 (t, J=7.6 Hz, 1H), 4.35 (t, J=7.2 Hz, 2H), 1.89 (m, 2H), 1.39-1.23 (m, 14H), 0.87 (t, J=6.8 Hz, 3H). $^{13}$C NMR (125 MHz, CDCl$_3$) δ=143.4, 141.6, 140.5, 127.3, 122.8, 122.5, 121.5, 120.9, 120.7, 117.2, 109.6, 108.2, 43.5, 31.8, 29.43, 29.40, 29.3, 29.2, 28.9, 27.2, 22.6, 14.1. HRMS-CI: $C_{22}H_{28}N_2O_2$ [M+H]$^+$, Calculated: 353.2224. Found: 353.2215.

Synthesis of 9-Decyl-3-iodo-6-nitrocarbazole (compound 4 of Scheme (E)): To a solution of 9-decyl-3-nitrocarbazole (9.1 g, 25.8 mmol) in CHCl$_3$ (100 mL) was added ICl (5 g, 31 mmol) stirred at room temperature for 1 h then refluxed for 30 min. The reaction progress was checked using $^1$H NMR. The reaction was quenched by adding an aqueous solution of sodium bisulfite and stirred for 20 min. The mixture was extracted with $CH_2Cl_2$, dried with $MgSO_4$, filtered then concentrated in vacuo to result in an orange solid product (12.1 g, 25.3 mmol, 98% yield). $^1$H NMR (400 MHz, CDCl$_3$) δ=8.97 (d, J=2.0 Hz, 1H), 8.48 (d, J=1.6 Hz, 1H), 8.40 (dd, J=9.0, 2.0 Hz, 1H), 7.82 (dd, J=8.6, 1.2 Hz, 1H), 7.41 (d, J=9.0 Hz, 1H), 7.26 (d, J=8.6 Hz, 1H), 4.32 (t, J=7.2 Hz, 2H), 1.87 (m, 2H), 1.33-1.23 (m, 14H), 0.87 (t, J=6.8 Hz, 3H). $^{13}$C NMR (100 MHz, CDCl$_3$)=143.2, 140.8, 140.7, 135.6, 129.7, 125.1, 122.1, 121.1, 117.3, 111.6, 108.5, 83.3, 43.7, 31.8, 29.42, 29.38, 29.3, 29.2, 28.8, 27.1, 22.6, 14.1. HRMS-CI: $C_{22}H_{27}IN_2O_2$[M+H]$^+$, Calculated: 479.1190. Found: 479.1188.

Synthesis of 3-Azido-9-decyl-6-iodocarbazole (compound 6 of Scheme (E)): A mixture of 9-decyl-3-iodo-6- nitrocarbazole (11.9 g, 24.9 mmol) and $SnCl_2.2H_2O$ (28 g, 124.4 mmol) in EtOAc (100 mL) and EtOH (100 mL) was refluxed overnight. After cooling to room temperature the reaction mixture was poured into an aqueous solution of $Na_2CO_3$ and stirred for 2 h, then extracted with EtOAc. The organic phased was dried with $MgSO_4$, filtered and concentrated in vacuo to give 3-amino-9-decyl-6-iodocarbazole (compound 5) as a light brown solid. This intermediate was dissolved in THF (100 mL) and $H_2SO_4$ (15 mL) in water (80 mL) was added under ice bath and stirred for 30 min. A solution of $NaNO_2$ (1.9 g, 27.4 mmol) in water (5 mL) was drop-wise added and the mixture was stirred for 1 h. A solution of $NaN_3$ (1.94 g, 29.9 mmol) in water (5 mL) was drop-wise added and stirred for 1 h at 0° C. The mixture was warmed to room temperature and stirred for 1 h. After removing THF under vacuo, the mixture was extracted with $CH_2Cl_2$. The organic phase was dried with $MgSO_4$ and concentrated in vacuo to give a light brown solid product (10.8 g, 22.8 mmol, 92% yield). $^1$H NMR (400 MHz, $CDCl_3$) δ=8.36 (d, J=1.6 Hz, 1H), 7.71 (dd, J=8.6, 2.0 Hz, 1H), 7.67 (d, J=2.3 Hz, 1H), 7.35 (d, J=9.0 Hz, 1H), 7.17 (d, J=8.6 Hz, 1H), 7.15 (dd, J=9.0, 2.0 Hz, 1H), 4.24 (t, J=7.2 Hz, 2H), 1.8 (m, 2H), 1.30-1.22 (m, 14H), 0.87 (t, J=6.6 Hz, 3H). $^{13}$C NMR (125 MHz, $CDCl_3$) δ=140.0, 137.8, 134.3, 131.5, 129.3, 124.4, 122.3, 117.9, 110.9, 110.3, 109.8, 81.2, 43.3, 31.8, 29.5, 29.4, 29.3, 29.2, 28.8, 27.2, 22.6, 14.1. HRMS-CI: $C_{22}H_{27}IN_4$ [M]$^+$, Calculated: 474.1275. Found: 474.1278.

Synthesis of 3-Azido-9-decyl-6-ethynylcarbazole (compound 7 of Scheme (E)): To a degassed solution of 3-azido-9-decyl-6-iodocarbazole (2.85 g, 6.01 mmol) and diisopropylamine (4.2 mL, 30 mmol) in THF (80 mL) was added $PdCl_2(PPh_3)_2$ (84 mg, 0.12 mmol), CuI (60 mg, 0.3 mmol) and trimethylsilylacetylene (1.3 mL, 9 mmol). The reaction mixture was stirred under argon atmosphere for 40 min and quenched with an aqueous solution of $NH_4Cl$. The mixture was extracted with EtOAc and the organic phase was dried with $MgSO_4$, filtered and concentrated in vacuo. The resulting viscous oil mixture was subjected to column chromatography on silica gel using hexanes to hexanes:EtOAc=97:3. The resulting light brown intermediate (3-azido-9-decyl-6-(trimethylsilyl)ethynylcarbazole) was dissolve in THF (30 mL) and MeOH (30 mL) and added a saturated solution of $K_2CO_3$ in MeOH (3 mL) and stirred overnight. The reaction was quenched with $NH_4Cl$ solution and extracted with $CH_2Cl_2$, dried with $MgSO_4$, filtered then concentrated in vacuo to give a light brown solid product (1.8 g, 4.8 mmol, 80% yield). $^1$H NMR (400 MHz, $CDCl_3$) δ=8.21 (s, 1H), 7.71 (d, J=2.0 Hz, 1H), 7.60 (d, J=8.2 Hz, 1H), 7.36 (d, J=8.6 Hz, 1H), 7.32 (d, J=8.6 Hz, 1H), 7.15 (dd, J=8.6, 2.3 Hz, 1H), 4.26 (t, J=7.2 Hz, 2H), 3.07 (s, 1H), 1.84 (m, 2H), 1.32-1.23 (m, 14H), 0.87 (t, J=6.8 Hz, 3H). $^{13}$C NMR (100 MHz, $CDCl_3$) δ=140.7, 138.2, 131.6, 130.1, 124.8, 123.2, 121.8, 117.7, 112.2, 110.3, 109.9, 108.8, 84.7, 75.3, 43.3, 31.8, 29.5, 29.4, 29.3, 29.2, 28.9, 27.2, 22.6, 14.1. HRMS-CI: $C_{24}H_{28}N_4$ [M+H]$^+$, Calculated: 373.2387. Found: 373.2379.

Synthesis of tridecyl-tricarbazolo-triazolophane (Formula (IB); "TC" of Scheme (E)): To a degassed solution of $CuSO_4$ (110 mg, 0.45 mmol), sodium ascorbate (180 mg, 0.9 mmol) and tris[(1-benzyl-1H-1,2,3-triazol-4-yl)methyl]amine (TBTA, 240 mg, 0.45 mmol) in THF (100 mL), EtOH (50 mL) and water (50 mL) was drop-wise added slowly for 6 h a solution of 3-azido-9-decyl-6-ethynylcarbazole (1.66 g, 4.46 mmol) in THF (40 mL) and EtOH (20 mL) at 70° C. The reaction was stirred for additional 2 h then cooled to room temperature. Organic solvents (THF and EtOH) were removed in vacuo. The mixture was extracted with $CHCl_3$ and the organic phased was washed with $NH_4Cl$ solution, dried with $MgSO_4$, filtered and concentrated in vacuo. The resulting solid mixture was subjected to column chromatography on silica gel using a eluent gradient from $CHCl_3$ to $CHCl_3$:EtOAc=95:5. The product was obtained as a light yellow solid (1.17 g, 1.05 mmol, 70% yield). $^1$H NMR (500 MHz, 2 mM, $CDCl_3$) δ=8.75 (s, 3H), 8.28 (s, 3H), 8.20 (d, J=8.2 Hz, 3H), 8.16 (d, J=8.6 Hz, 3H), 8.12 (s, 3H), 7.22 (d, J=8.6 Hz, 6H), 4.14 (t, J=6.6 Hz, 6H), 1.81 (m, 6H), 1.34-1.25 (m, 42H), 0.86 (t, J=6.4 Hz, 9H). $^{13}$C NMR (125 MHz, 10 mM, $CDCl_3$) δ=149.7, 140.8, 139.9, 129.2, 124.0, 122.5, 122.4, 121.9, 118.3, 117.7, 117.5, 110.6, 109.4, 109.2, 43.4, 31.8, 29.5, 29.4, 29.3, 27.3, 22.7, 14.1 (two carbon peaks of the decyl-groups are overlapping with others in the 29.5-29.2 ppm region). HRMS-ESI: $C_{72}H_{84}N_{12}$ [M+PF$_6$]$^-$, Calculated: 1261.6584. Found: 1261.6559.

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

The invention claimed is:
1. A composition comprising a tricarbazole triazolophane (tricarb) selected from one of the following:

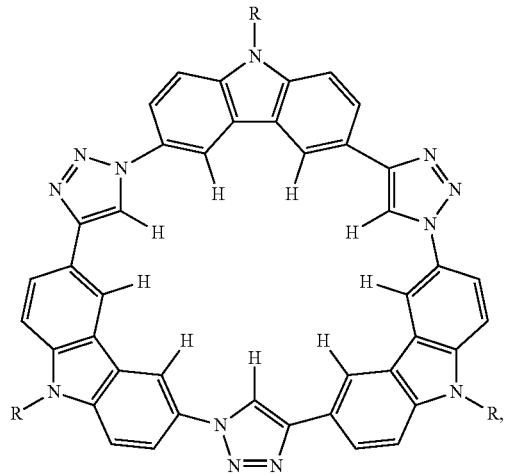
(I)

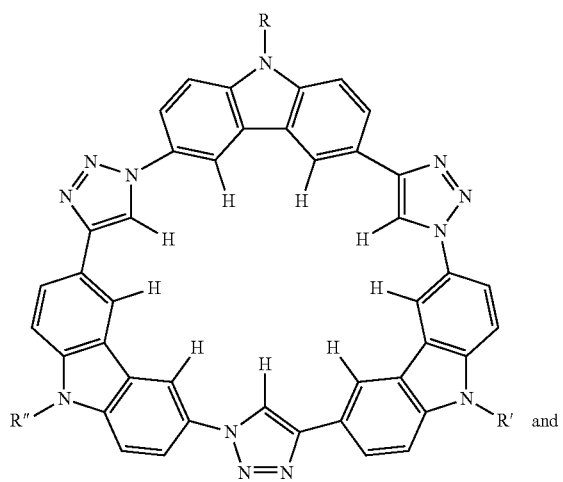
(II)

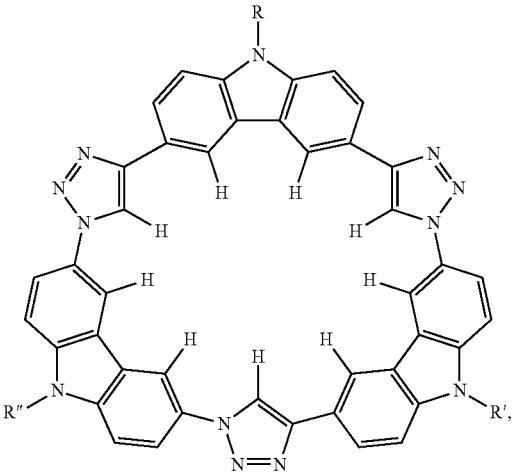
(III)

or a combination thereof,
wherein R of Formula (I) is selected from a group consisting of alkyl, alkyl-substituted phenyl, and substituted glycol, or a combination thereof, and R, R' and R" of Formulas (II) and (III) are independently selected from a group consisting of alkyl, alkyl-substituted phenyl, and substituted glycol, or a combination thereof.

2. The composition of claim 1, wherein R of Formula (I) is selected from a group consisting of $C_6H_{13}$ (IA), $C_{10}H_{21}$ (IB), $C_{18}H_{37}$ (IC), di-tert-butyl phenyl (ID), and triethylene glycol (IE), or a combination thereof:

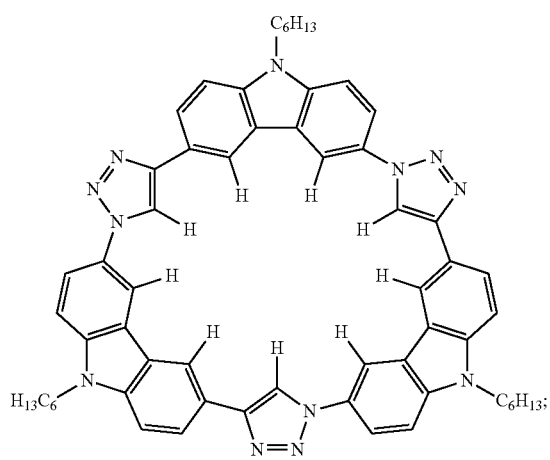
(IA)

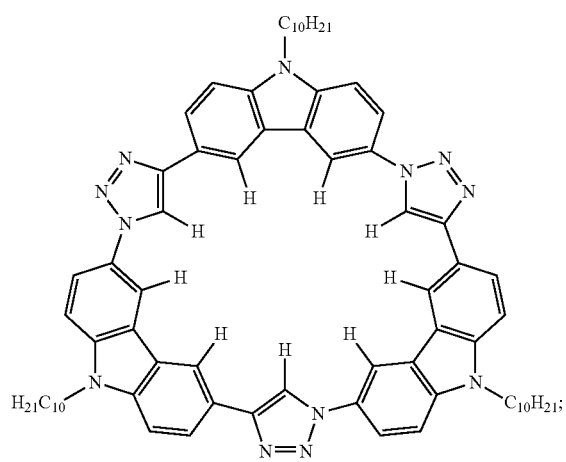
(IB)

-continued
(IC)
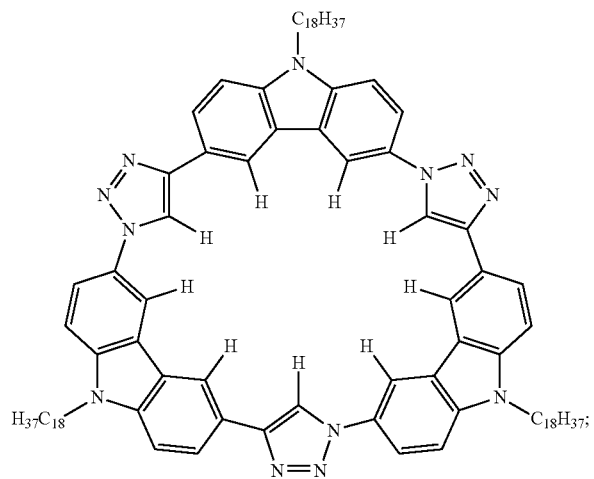
(ID)
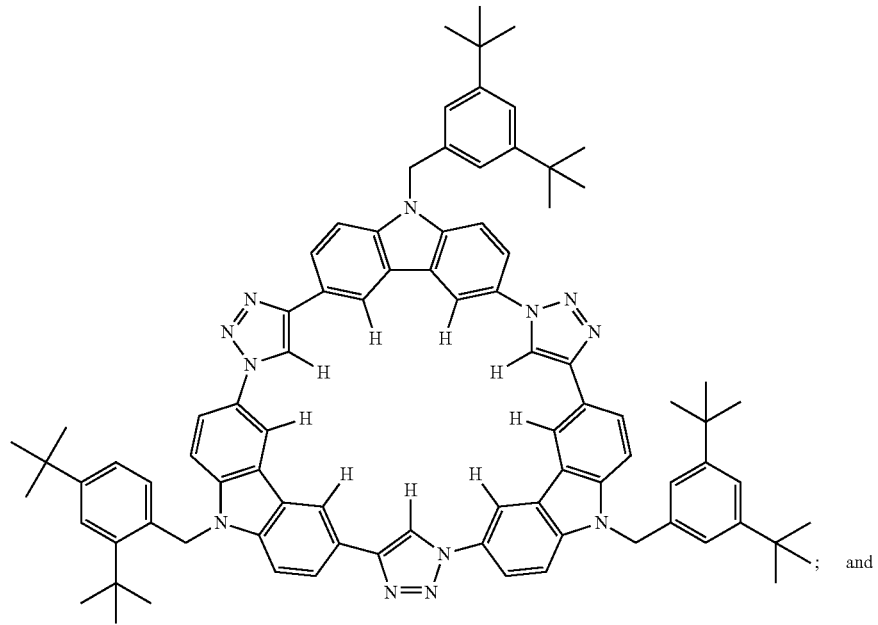
; and (IE)

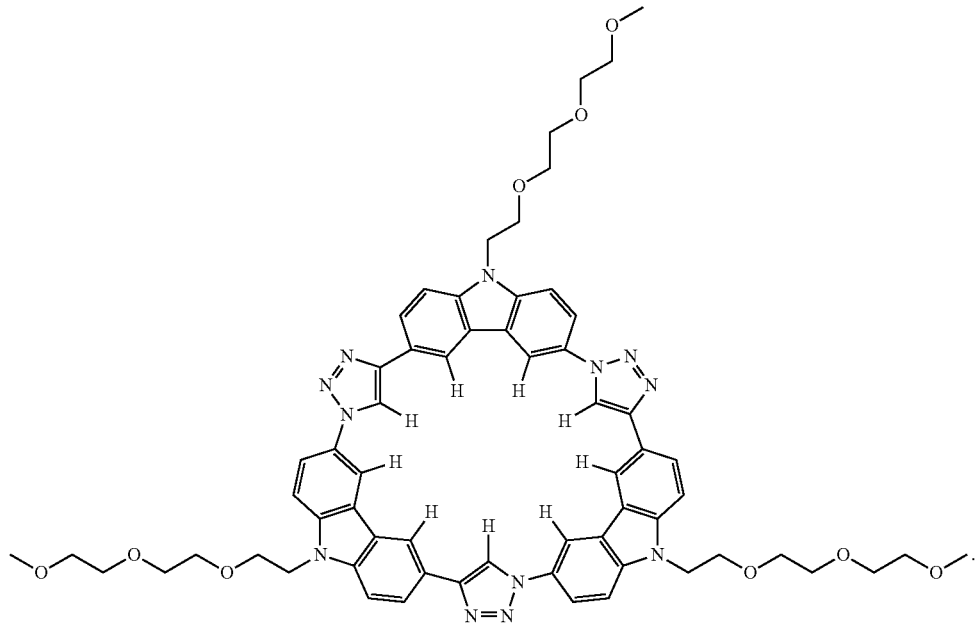

3. The composition of claim 1, wherein R is $C_{10}H_{21}$ (IB):

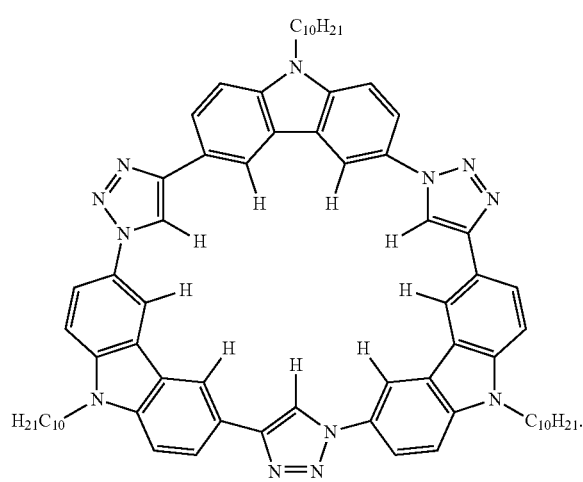

(IB)

4. A complex, comprising:
a composition of claim 1, and
an anion,
wherein the composition is bound to the anion.

5. The complex of claim 4, wherein the anion is selected from a group consisting of $ClO_4^-$, $ReO_4^-$, $PF_6^-$, $SbF_6^-$, $FeCl_4^-$, mesylate ($CH_3SO_3^-$), triflate ($CF_3SO_3^-$), arsenate ($AsO_4^{3-}$), hexafluoroarsenate ($AsF_6^-$), tetrachloroaluminate ($AlCl_4^-$), phosphate ($PO_4^{3-}$), hydrogenophosphate ($HPO_4^{2-}$), dihydrogenophosphate ($H_2PO_4^-$), sulfate ($SO_4^{2-}$), hydrogen sulfate ($HSO_4^-$), tetracyanoborate ($B(CN)_4^-$), a halide ($F^-$, $Cl^-$, $Br^-$, $I^-$), cyanide, perbromate ($BrO_4^-$), periodate ($IO_4^-$), bifluoride ($HF_2^-$), pertechnetate ($TcO_4^-$), monosubstituted phosphate esters ($RPO_4^{2-}$), disubstituted phosphate esters ($R_2PO_4^-$), organosulfonates ($RSO_3^-$), thiocyanate, ($SCN^-$), azide ($N_3^-$), triiodide ($I_3^-$), carbonate ($CO_3^{2-}$), monohydrogen carbonate ($HCO_3^-$), iron tetrachlorate, gold dicyanate ($Au(CN)_2^-$), acetate ($CH_3CO_2^-$), uranium hexafluoride ($UF_6^-$), sulfide ($S^{2-}$), platinum hexachlorate ($PtCl_6^{2-}$), and $S_2^{2-}$, $S_4^{2-}$, $S_6^{2-}$, $S_8^{2-}$ and $S_n^{2-}$, where n is an even number, or a combination thereof, including mono- and poly-protonated forms, or a combination of the foregoing anions thereof.

6. The complex of claim 4, wherein a ratio of the composition comprising a tricarb to the anion is selected from 1:1 (tricarb:anion), 2:1 (tricarb:anion), and 3:2 (tricarb:anion).

7. The complex of claim 4, wherein the anion displays one of a binding affinity parameter of log $\beta_2$ greater than 7 or a positive cooperativity greater than 5.

8. A method of binding an anion, comprising:
contacting the anion with a composition of claim 1.

9. A method of removing an anion from a mixture, comprising:
contacting the mixture with a composition of claim 1 to form a complex comprising the anion and the composition; and
separating the complex from the mixture.

10. A film comprising a composition of claim 1.

11. A method of binding an anion, comprising:
contacting the anion with a film of claim 10.

12. A method of removing an anion from a mixture, comprising:
contacting the mixture with a film comprising the composition of claim 1 to form a complex of the anion and the film or a dissociated dimer of a tricarb thereof, wherein the tricarb comprises the composition of claim 1; and
separating from the mixture the complex of the anion and the film or the dissociated dimer of a tricarb thereof.

13. A method of controlling the thickness of a film comprising the composition of claim 1, wherein the thickness of the film is obtained by varying one of the following parameters:

a concentration of the composition of claim 1, the amount of anions, and at least one substituent of the composition of claim 1.

14. A composition comprising the tricarb according to claim 1, wherein the tricarb is oxidized.

15. A composition comprising the complex according to claim 6, wherein the tricarb is oxidized.

16. A method of oxidation, comprising contacting the composition of claim 1 with an electrode to which is applied a positive voltage.

17. A method of oxidation, comprising contacting the complex of claim 6 with an electrode to which is applied a positive voltage.

18. A method of oxidation, comprising contacting the composition of claim 1 with an oxidizing agent.

19. A method of oxidation, comprising contacting the complex of claim 6 with an oxidizing agent.

\* \* \* \* \*